(12) United States Patent
Srienc et al.

(10) Patent No.: US 8,409,509 B2
(45) Date of Patent: Apr. 2, 2013

(54) SYSTEMS AND METHODS FOR ANALYZING A PARTICULATE

(75) Inventors: Friedrich Srienc, Lake Elmo, MN (US); Greg Sitton, Minneapolis, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 740 days.

(21) Appl. No.: 12/102,851

(22) Filed: Apr. 14, 2008

(65) Prior Publication Data
US 2008/0268469 A1 Oct. 30, 2008

Related U.S. Application Data

(60) Provisional application No. 60/911,361, filed on Apr. 12, 2007.

(51) Int. Cl.
*G01N 21/00* (2006.01)
*G01N 31/00* (2006.01)

(52) U.S. Cl. ............... 422/82.11; 422/412; 422/417; 422/68.1; 422/81; 422/82.05; 422/504; 422/505; 435/286.5; 435/286.7; 436/165; 436/172; 436/173

(58) Field of Classification Search .............. 422/417, 422/68.1, 81, 82.05, 82.08, 82.09, 504, 505, 422/412, 82.11; 435/7.1, 7.2, 286.5, 286.7, 435/287.2, 287.3; 436/517, 165, 172, 173; 356/72, 318, 344
See application file for complete search history.

(56) References Cited

U.S. PATENT DOCUMENTS

| | | | |
|---|---|---|---|
| 5,325,169 A | 6/1994 | Nakamoto et al. | |
| 5,456,102 A | 10/1995 | Moorehead | |
| 5,821,066 A | 10/1998 | Pyle et al. | |
| 6,245,506 B1 | 6/2001 | Laugharn, Jr. et al. | |
| 6,884,624 B1 | 4/2005 | Gourley | |
| 7,059,766 B2 | 6/2006 | Lemoine et al. | |
| 7,158,227 B2 * | 1/2007 | Couderc et al. | ............... 356/318 |
| 7,161,665 B2 | 1/2007 | Johnson | |
| 7,201,875 B2 | 4/2007 | Norton et al. | |
| 7,776,583 B2 * | 8/2010 | Billadeau et al. | ........... 435/286.5 |
| 2002/0028434 A1 | 3/2002 | Goix | |
| 2004/0136870 A1 | 7/2004 | Kochy et al. | |

(Continued)

FOREIGN PATENT DOCUMENTS

| | | |
|---|---|---|
| WO | WO 00/68689 | 11/2000 |
| WO | WO 01/88176 | 11/2001 |

(Continued)

OTHER PUBLICATIONS

Brando et al., "Cytofluorometric methods for assessing absolute numbers of cell subsets in blood," *Cytometry*, 2000, 42(6):327-346.

(Continued)

*Primary Examiner* — Gail R Gabel
(74) *Attorney, Agent, or Firm* — Fish & Richardson P.C.

(57) ABSTRACT

Systems and methods are provided for analyzing particulates. A liquid having a plurality of particulates substantially linearly ordered in a streamline can be externally controlled to provide flow in first and second directions, where, generally, the first direction is opposite to the second direction. A target particulate can be measured from the plurality of particulates at or near a measurement area while the liquid flows in the first flow direction. The flow direction can be reversed and measured at the measurement area while flowing in the second direction. The particulates substantially retain the same linear order during at least one cycle, a cycle being defined by movement in the first direction followed by movement in the second direction.

6 Claims, 27 Drawing Sheets

U.S. PATENT DOCUMENTS

2005/0070005 A1  3/2005 Keller
2006/0050596 A1  3/2006 Abassi et al.

FOREIGN PATENT DOCUMENTS

WO  WO 02/29106     4/2002
WO  WO 2004/005531  1/2004
WO  WO 2006/017635  2/2006

OTHER PUBLICATIONS

Clay et al., "Assays for monitoring cellular immune responses to active immunotherapy of cancer," . Clin. Cancer Res., 2001, 7(5):1127-1135.
Douglas-Hamilton et al., "Capillary-loaded particle fluid dynamics: effect on estimation of sperm concentration," J. Andrology, 2005, 26:115-122.
Droste et al., "Noninvasive measurement of cell volume changes by negative staining," J. Biomed. Optics, 2005, 10:1-10.
Farmer et al., "Flow cytometric assays for monitoring production of recombinant HIV-1 gp160 in insect cells infected with a baculovirus expression vector," J. Virol. Meth., 1989, 26(3):279-290.
Gallard et al., "Tracking T cell clonotypes in complex T lymphocyte populations by real-time quantitative PCR using fluorogenic complementarity-determining region-3-specific probes," J. Immunol. Meth., 2002, 270(2):269-280.
Gervaix et al., "A new reporter cell line to monitor HIV infection and drug susceptibility in vitro," Proc. Natl. Acad. Sci. USA, 1997, 94(9):4653-4658.
Healy et al., "Flow cytometric detection of tandem repeat mutations induced by various chemical classes," Mutation Res., 2006, 598:85-102.
Hinson et al., "A microsample collection device for electrostatically sorted cells or particles and its preparative use for biochemical analysis," Cytometry, 1982, 2(6):390-394.
Ho and Liu, "Micro T-switches for cell sorting applications," ASME International Mechanical Enginerering Congress and Exposition, Nov. 13-19, 2004, Anaheim, CA, Abstract.
Huang et al., "Transport, location, and quantal release monitoring of single cells on a microfluidic device," Anal. Chem., 2004, 76(2):483-488.
Huerta et al., "Flow Cytometry monitoring of cell recruitment into syncytia induced by HIV-envelope expressing cells," Biochem. Soc. Trans., 2004, 32:178A, Abstract No. R406.
Johnson et al., "Evaluation of four alternative methodologies for determination of absolute CD4+lymphocyte counts," J. Acquired Immune Deficiency Syndromes and Human Retrovirology, 1995, 10(5):522-530.
Kruyt et al., "Noninvasive Real-Time in-Vivo Monitoring of Cells in Tissue Engineered Constructs," Tissue Engineering, 2003, 9(4):843, Abstract No. 197.
Monica et al., "Monitoring Adenovirus Infections with On-Line and Off-Line Methods," Biotechnol. Prog., 2000, 16(5):866-871.
Mosley et al., "Lymphocyte transendothelial brain migration in murine HIV-1 encephalitis: Tracking cell movement by single photon emission computed tomography," J. Neurovirol., 2003, 9:124-125.
Muraro et al., "Molecular tracking of antigen-specific T cell clones in neurological immune-mediated disorders," Brain, 2003, 126:20-31.
Nassiri et al., "Flow cytometric evaluation of the cytotoxicity of novel antiviral compounds," Cytometry, 1990, 11(3):411-417.
O'Gorman et al., "Inter- and intrainstitutional evaluation of automated volumetric capillary cytometry for the quantitation of CD4- and CD8-positive T lymphocytes in the peripheral blood of persons infected with human immunodeficiency virus," Clin. Diagn. Lab. Immunol., 1997, 4(2):173-179.
O'Gorman et al., "Volumetric capillary cytometry (VCC): Accuracy and precision of CD4 and CD8T cell measurements within and between laboratories," Eleventh International Conference on Aids, Jul. 7-12, 1996, Vancouver, British Columbia, Canada, Abstract.
Ohashi et al., "Arrested maturing multivesicular endosomes observed in a Chinese hamster ovary cell mutant, LEX2, isolated by repeated flow-cytometric cell sorting," J. Cell Science, 2000, 113:2187-2205.
Schols et al., "Novel Flow Cytometric Method to Monitor Cell Fusion Between HIV-Infected and Uninfected CD4+Cells," J. Cell. Biochem., 1990, 14D:177, Abstract No. L542.
Shirasaki et al., "On-Chip Cell Sorting System Using Laser-Induced Heating of a Thermoreversible Gelation Polymer to Control Flow," Anal. Chem., 2006, 78(3):695-701.
Shoemaker et al., "Multiple sampling in single-cell enzyme assays using CE-laser-induced fluorescence to monitor reaction progress," Anal. Chem., 2005, 77(10):3132-3137.
Szabo et al., "Millimeter wave induced reversible externalization of phosphatidylserine molecules in cells exposed in vitro," Bioelectromagnetics, 2006, 27(3):233-244.
Tibbe et al., "Optical tracking and detection of immunomagnetically selected and aligned cells," Nat. Biotechnol., 1999, 17(12):1210-1213.
van den Brandt et al., "Lentivirally generated eGFP-transgenic rats allow efficient cell tracking in vivo," Genesis, 2004, 39(2):94-99.
Wieder et al., "Optimization of reporter cells for expression profiling in a microfluidic device," Biomedical Microdevices, 2005, 7(3):213-222.
Zurgil et al., "Reactivity of peripheral blood lymphocytes to oxidized low-density lipoprotein: a novel system to estimate atherosclerosis employing the Cellscan," Clin. Cardiol., 1999, 22(8):526-532.
Auton, "The lift force on a spherical body in a rotational flow," J. Fluid Mech., 1987, 83:199-218.
Block et al., "Slit scanning of Saccharomyces cerevisiae cells: quantification of asymmetric cell division and cell cycle progression in asynchronous culture," Biotechnol. Prog., 1990, 6(6):504-512.
Brehm-Stecher and Johnson, "Single-Cell Microbiology: Tools, Technologies, and Applications," Microbiol. Mol. Biol. Rev., 2004, 68(3):538-559.
Bretherton, "Slow viscous motion round a cylinder in a simple shear," J. Fluid Mech., 1962, 12:591-613.
Fredrickson et al., "Statistics and Dynamics of Procaryotic Cell Populations," Math Biosci., 1967,1:327-374.
Goldsmith and Mason, "The flow of suspensions through tubes. Part 1. Single spheres, rods and discs," J. Colloid Sci., 1962, 17:448-476.
Goldsmith and Mason, "The microrheology of dispersions," Rheology, 1967, 4:85-.
Joseph and Ocando, "Slip Velocity and Lift," J. Fluid Mech., 2002, 454:263-286.
Kromenaker and Srienc, "Cell-cycle dependent polypeptide accumulation by producer and non-producer murine hybridoma cell lines: a population analysis," Biotechnol. Bioeng., 1991, 38:665-677.
Leighton and Acrivos, "The Lift on a Small Sphere Touching a Plane in the Presence of a Simple Shear Flow," Z. Agnew. Math Phys., 1985, 36:174-178.
Li et al., "Transversely illuminated liquid core waveguide based fluorescence detection. Fluorometric flow injection determination of aqueous ammonium/ammonia," Talanta, 1999, 50:617-623.
Li et al., "Force evaluations in lattice Boltzmann simulations with moving boundaries in two dimensions," Physical Review E, 2004, 70:026701.
Mariella Jr. et al., "Flow-stream Waveguide for Collection of Perpendicular Light Scatter in Flow Cytometry," Cytometry, 1996, 24:27-31.
Matas et al., "Inertial migration of rigid spherical particulates in Poiseuille flow," J. Fluid Mech., 2004, 515:171-195.
Mclaughlin, "Inertial migration of a small sphere in linear shear flows," J. Fluid Mech., 1991, 224:261-274.
Patankar et al., "Lift-off of a single particle in Newtonian and viscoelastic fluids by direct numerical simulation," J. Fluid Mech., 2001, 438:67-100.
Rubinow and Keller, "The Transverse Force on a Spinning Sphere Moving in a Viscous Fluid," J. Fluid Mech., 1961, 11:447-459.
Saffman, "The lift on a small sphere in a slow shear flow," J. Fluid Mech., 1965, 22:385-400.
Segrè and Silberberg, "Behavior of macroscopic rigid spheres in Poiseuille flow: Part I," J. Fluid Mech., 1962, 14:136-157.

Segrè and Silberberg, "Radial Poiseuille flow of suspensions," *Nature*, 1961, 189:209-223.

Shapiro and Hercher, "Flow Cytometers Using Optical Waveguides in Place of Lenses for Specimen Illumination and Light Collection," *Cytometry*, 1986, 7:221-223.

Srienc and Dien, "Kinetics of the cell cycle of *Saccharomyces cerevisiae*," *Ann. N. Y. Acad. Sci.*, 1992, 665:59-71.

Wang and Joseph, "Lift forces on a cylindrical particle in plane Poiseuille flow of shear thinning fluids," *Physics Fluids*, 2003, 15:2267-2278.

Yang et al., "Lift Force on a Sphere in Tube Flow," *J. Fluid Mech.*, 2005, 540:109-131.

* cited by examiner

SYSTEMS AND METHODS FOR ANALYZING A PARTICULATE

CROSS REFERENCE TO RELATED APPLICATIONS

This application claims priority under 35 U.S.C. §119(e) of U.S. Application Number 60911361, filed Apr. 12, 2007, the entire contents of which are incorporated herein by reference.

TECHNICAL FIELD

This disclosure relates to systems and methods for analyzing particulates, and more particularly to systems and methods for analyzing particulates in a flow stream.

BACKGROUND

Some scientific instruments are configured to analyze small particulates with high rates of particulate throughput. Flow cytometry is one example of an analytical tool that can be used to count, examine, and sort microscopic particulates suspended in a stream of moving fluid. Particulates may include living cells, and therefore the method is used in many areas of the life sciences, including biology, pathology, immunology, and medicine. The throughput of modern cytometers can exceed thousands of particulate analyses per second, and thus provide rapid results in performing complex experiments involving cellular recognition, growth, or other properties.

SUMMARY

In general, according to one embodiment, a particulate analyzer (PA) is described. The PA allows one or more particulates to be measured in both forward and reverse flow directions. The PA can, in some embodiments, maintain an order of the particulates for extended periods of time. A streamline of particulates (a "plug") can be formed within a volume of a fluid by, e.g., oscillating the fluid back-and-forth within a capillary; the plug can be controlled so as to oscillate through a measurement area for analysis.

In one general aspect, a method is provided. In one embodiment of the method, the method includes providing an apparatus. The apparatus includes a liquid having therein a plurality of particulates, the particulates being substantially linearly ordered in a streamline of the liquid, the liquid being externally controllable to provide flow in a first direction and flow in a second direction that is substantially opposite to the first direction. The method further includes measuring one or more target particulates from the plurality of particulates at or near a measurement area while flowing the liquid in the first flow direction. The method also includes measuring one or more target particulates from the plurality of particulates at or near a measurement area while flowing the liquid in the second flow direction. The particulates substantially retain the same linear order as they pass through the measurement area during at least one cycle, the cycle defined by movement in the first direction followed by movement in the second direction.

As used herein, "measuring" one or more target particulates means detecting or determining one or more qualitative (e.g., presence or absence of a label) or quantitative aspects or characteristics associated with such particulates.

In one embodiment of the method, the particulates substantially retain the same linear order during more than one cycle. In one implementation, the number of cycles is at least 5 cycles. In an alternative implementation, the number of cycles is at least 10 cycles. In another implementation, the number of cycles is at least 100 cycles. In yet another implementation, the number of cycles is at least 1000 cycles.

One embodiment provides that one or more particulates are measured during each of the cycles.

In an alternative embodiment, the particulate is a biological cell, and in some cases the cell is a yeast cell.

In one embodiment, the measurement area is a focal point or plane of a laser or camera.

In one embodiment, measurement includes measuring scattered light from the one or more target particulates. In an alternative embodiment, measurement includes capturing a photographic image of the one or more target particulates.

In various implementations, the method further includes measuring multiple particulates in a first flow direction, followed by reversing the flow direction and measuring the multiple particulates in reverse order.

In some implementations, one or more of the particulates are labeled. In an exemplary implementation, the label is a fluorescent label.

In one embodiment, the apparatus includes a capillary-waveguide configured to channel energy originating from the measurement area to a detector distal to the measurement area, wherein the liquid is confined within the capillary-waveguide. An exemplary capillary-waveguide is comprised of an amorphous fluoropolymer.

In one embodiment, energy is electromagnetic or acoustic energy.

In another embodiment, the apparatus further includes a reflective optical component configured to reflect energy from a first end of the capillary-waveguide to a second end of the capillary waveguide. In one implementation, the apparatus further includes a coupler that transmits energy from within the capillary-waveguide to a medium external to the capillary-waveguide. In one embodiment, the medium is a fiber optic that guides energy from the coupler to a detector, wherein the fiber optic is in optical communication with the detector.

Some embodiments further include selectively adding or removing a particulate from the plurality of particulates. In one alternative embodiment, adding or removing a particulate includes providing a cross-flow fluid that merges with the streamline at an angle, the cross-flow fluid being controllable by an actuator. In one embodiment, the cross-flow fluid includes particulates that are the same or different as the one or more target particulates.

In an alternative embodiment, the method further includes controlling an environmental condition of the plurality of particulates. The environmental condition is, according to one embodiment, one or more of temperature, pH, salinity, light conditions, exposure to magnetic fields, exposure to a pharmaceutical compound, available oxygen, fermentable and non-fermentable sugars, lipids, or polypeptides.

In one embodiment, the method further includes determining a cell population balance equation from the measuring the target particulate in the first direction and the second direction; and wherein the particulate is a cell.

In one embodiment, the method further includes determining a cell partitioning function from the measuring the target particulate in the first direction and the second direction; and wherein the particulate is cell.

An alternative embodiment provides that measuring includes providing a light beam with a propagation axis orthogonal to a flow axis of the liquid, providing a detector adapted to receive measurement signals, and detecting the measurement signals resulting from interaction between the light beam and the target particulate or moiety attached to a surface of the target particulate. In one variation of the embodiment, the light beam is output from a laser. In another variation, the detector is a charge-coupled device or array; in another variation the detector is a camera. Certain embodiments provide that the measurement signals comprise one or all of attenuation, wavelength shift, collimation, or mode structure.

In one embodiment, the apparatus includes a capillary adapted to provide fluid flow, and wherein the liquid is contained within the capillary. In various implementations, the capillary has an inner diameter between about 0.010 mm and about 1 cm.

In various implementations of one or more embodiments, the external controllability to provide flow in the first and the second directions is accomplished by providing a pump, and controlling the pump to provide an oscillatory pressure differential between the inlet end and the output end of the capillary. The pump includes an inlet port and an outlet port and wherein the pump is adapted to provide positive or negative pressure to both inlet port and outlet port. The inlet port is connected to an input end of a capillary, and the outlet port is connected to an output end of the capillary. In one variation of the embodiment, the pump is a positive displacement pump.

In one embodiment, the method is a cytometry method.

In some implementations, the capillary is a gas-permeable capillary, and a condition of the fluid is alterable by introducing a gas into the fluid through the gas-permeable capillary. In some cases, gas is one or more of oxygen, carbon dioxide, and nitrogen In some implementations, the apparatus further includes one or more individually-controllable buffer pumps that allow buffer solutions to be introduced into the capillary while retaining the plurality of particulates within the capillary.

Some embodiments provide that the apparatus further includes a porous capillary configured to allow solute exchange between the porous capillary and the fluid within the capillary.

In general, according to one aspect, a system for analyzing one or more particulates is provided. In one embodiment, the system includes a capillary having a lumen configured for fluid flow, the capillary having an index of refraction less than that of the fluid, and configured to guide energy scattered or emitted from one or more particulates in a measurement area to a signal collection assembly located distal to the measurement area. The system further includes an energy source that imparts energy to the measurement area, and a pump system configured to apply a selectable pressure to an end of the capillary to cause the one or more particulates to move back and forth across the measurement area.

In one variation of the system, energy is light energy from a laser.

In one variation of the system, the capillary is a hollow-bore waveguide.

In yet another variation, the system further includes a coupler fixedly attached to the capillary, wherein the coupler provides fluid flow from the capillary to a tube that flows the fluid away from the capillary, and also provides for the energy to be transmitted from the capillary to an energy conduit. The energy conduit is a fiber-optic waveguide that transmits light energy from the coupler to a light detector in some embodiments.

In general, according to another aspect, a method for sorting cells is provided. In one embodiment, the method includes providing a capillary, the capillary containing therein a liquid including a plurality of cells, the cells being substantially ordered in a streamline of the liquid, the liquid being externally controlled to provide flow along the capillary in a first direction and flow along the capillary in a second flow direction that is substantially opposite to the first direction. The method further includes measuring one or more target cells from the plurality of cells at or near a measurement area while the cells are flowing in the first flow direction. The method further includes measuring one or more target cells from the plurality of cells at or near a measurement area while the cells are flowing in the second flow direction. The method further includes providing a flow-switch configured to selectably channel the liquid containing the one or more target cells in a selectable direction. The one or more target cells remains substantially linearly ordered within the capillary during flow in the first flow direction and flow in the second flow direction.

In some embodiments, the capillary is a waveguide-capillary.

In some embodiments, the measurement area is a focal point or plane of a laser or camera.

In some embodiments the measurement includes detecting scattered light from the target cells.

In alternative embodiments, the measurement includes capturing a photographic image of the target cell.

In some cases, the method provides that multiple cells are measured in order in a first flow direction, followed by measuring the multiple cells in reverse order upon reversing the flow direction; in some cases one or more cells of the plurality of cells are uniquely identifiable by a label associated with the one or more cells.

In various implementations, the label is a fluorescent molecule; in some implementations the label is a Raman-active compound, and the measuring includes measuring a Raman spectrum of the label.

In one embodiment of the method, measuring a target cell includes providing a light beam with a propagation axis orthogonal to a flow axis of the liquid, providing a detector adapted to receive measurement signals, and detecting the measurement signals resulting from interaction between the light beam and the target cell or a label attached to the target cell.

In some embodiments, the light beam is an output from a laser.

In some embodiments, the light detector is a charge-coupled device or array.

In one embodiment, the detector is a camera.

In one embodiment, detecting includes one of measuring attenuation, wavelength shift, collimation, spectral properties, or mode structure.

In some cases, detecting the measurement signals includes detecting scattered light from the target cells.

In various implementations of the method, the liquid is contained within a capillary configured to provide fluid flow. The capillary has an internal diameter between 0.010 mm and 1.0 cm in some embodiments.

In some embodiments, providing flow in the first and the second directions is accomplished by providing a pump. The pump includes an inlet port and an outlet port, and is adapted to provide positive or negative pressure to both inlet port and outlet port. Further, the method includes connecting the inlet port to an input end of a capillary, and connecting the outlet port to an output end of the capillary, and controlling the pump to provide an oscillatory pressure differential between the inlet end and the output end of the capillary to cause the liquid to flow in substantially opposite directions.

In one embodiment, the pump is a positive displacement pump.

In one embodiment, the plurality of cells is distinguished by attaching to the cells a spectroscopically-detectable moiety. The spectroscopically-detectable moiety is a fluorescent, or Raman-active molecule, polypeptide, inorganic cluster, or crystal, in some implementations. In an alternative embodiment, the spectroscopically-detectable moiety is a nanocrystal.

In some cases, target cells are distinguishable based on cell size, and in some embodiments, the method is a cytometry method.

In yet another general aspect, a system is provided. In one embodiment of the system, the system includes a capillary tube having at least two ends, a fluid contained within the capillary tube, the fluid including suspended particulates in a streamline of the fluid, a pump system configured to apply a selectable pressure to an end of the capillary tube, and a signal collection assembly configured to detect one or more target particulates at a measurement area within the fluid. The pump system is controllable to cause the one or more target particulates to move back and forth across the measurement area, and wherein the signal collection assembly is adapted to record signals from the one or more particulates as the one or more particulates move back and forth across the measurement area; and wherein the particulates substantially retain the same linear order as they pass through the measurement area during the back and forth movement.

In one system alternative, the capillary tube is a waveguide-capillary. In some cases the capillary has an internal diameter between 0.010 mm and 1.0 cm.

In one embodiment, the pump system includes a positive-displacement pump.

In one embodiment, a signal collection assembly includes a charge-coupled device or array. In an alternative embodiment, the signal collection assembly includes a camera adapted to collect images of the target particulate at or near the measurement area. In one embodiment, the measurement area is a focal point or plane of a laser or camera.

In one implementation, signals comprise one or all of beam attenuation, wavelength shift, collimation, or mode structure. In another implementation, the signals comprise light scattering from the target particulates.

In an alternative embodiment, the system is a system adapted for cytometry.

In yet another general aspect, a method for characterizing a cell population dynamic is provided. In one embodiment, the method includes providing a liquid contained in a capillary, the liquid including a plurality of biological cells, the cells being substantially ordered in a streamline of the liquid. The method further includes providing controllable pressure to the capillary to cause the liquid to flow in a first flow direction and in a second flow direction, the second flow direction being substantially opposite to the first flow direction. The method further includes measuring a physiological or morphological characteristic of one or more target cells from the plurality of living cells at a measurement area while flowing in the first flow direction. The method further includes measuring a physiological or morphological characteristic of one or more target cells from the plurality of living cells at a measurement area while flowing in the second flow direction. The method further includes characterizing a cell population dynamic using data from the measured physiological or morphological characteristic of the one or more target cells. The linear order of the plurality of biological cells remains substantially unchanged during the measurements.

In one embodiment, providing a pressure source adapted to provide flow in the first and the second directions includes providing a pump. The pump includes an inlet port and an outlet port, and is adapted to provide positive or negative pressure to both inlet port and outlet port. The inlet port is connected to an input end of the capillary, and the outlet port is connected to an output end of the capillary. The method further includes controlling the pump to provide an oscillatory pressure differential between the inlet end and the output end of the capillary to cause the liquid to alternate flow in the first and the second flow directions.

In some cases, measuring a physiological or morphological characteristic of the one or more target cells includes measuring a single cell growth rate function or a division rate function.

In one embodiment, the method further includes providing a dynamic environment for the cells by altering a characteristic of the liquid. In various alternative embodiments, the characteristic includes one or more of: temperature, pH, salinity, light conditions, exposure to magnetic fields, exposure to a chemical compound, available oxygen, fermentable and non-fermentable sugars, lipids, or polypeptides.

In one embodiment, the method is a cytometry method.

In general, according to yet another aspect, a method for evaluating cellular growth is provided. In one embodiment, the method includes providing a liquid comprising living cells, the cells being substantially linearly ordered in a streamline of the liquid, the liquid being externally controllable to provide flow in a first flow direction and in a second flow direction that is substantially opposite to the first flow direction. A size of one or more target cells is measured within the liquid at a measurement area while flowing in the first flow direction. A size of one or more target cells is measured within the liquid at a measurement area while flowing in the second flow direction. The cells substantially retain the same linear order as they pass through the measurement area during at least one cycle, the cycle defined by movement in the first direction followed by movement in the second direction.

In one implementation of the method, the liquid is contained in a capillary.

In one embodiment, providing a pressure source adapted to provide flow in the first and the second directions includes providing a pump. The pump includes an inlet port and an outlet port, and the pump is adapted to provide positive or negative pressure to both inlet port and outlet port. The method further includes connecting the inlet port to an input end of a capillary containing the liquid, and the outlet port to an output end of the capillary, and controlling the pump to provide an oscillatory pressure differential between the inlet end and the output end of the capillary to cause the liquid to alternately flow in the first direction and in the second direction.

In some cases, the measurement area is a focal point or plane of a camera or laser.

In one embodiment, the measurement area is a focal point or plane of a laser, and the measuring a size of the one or more target cells includes detecting a pattern of scattered radiation from the measurement area on a charge-coupled device array and calculating the size of the one or more target cells based on the pattern.

In one embodiment the method further includes providing a dynamic environment for the living cells by altering a characteristic of the liquid. In some cases the characteristic includes one or more of temperature, pH, salinity, light conditions, exposure to magnetic fields, exposure to a chemical compound, available oxygen, fermentable and non-fermentable sugars, lipids, or polypeptides.

In one embodiment of the method, the method is a cytometry method.

In yet another general aspect, a method for evaluating response of a cell to a compound is provided. In one embodiment, the method includes providing a liquid that includes a plurality of cells substantially ordered in a streamline of the liquid, providing the compound within the liquid, measuring a target cell within the liquid while the liquid flows in a first flow direction, reversing the flow direction and measuring the target cell while the liquid flows in a second direction, opposite to the first flow direction, and evaluating the response based on the measurements. The particulates substantially retain the same linear order as they pass through the measurement area during at least one cycle, the cycle defined by movement in the first direction followed by movement in the second direction.

In one embodiment, the compound is a pharmaceutical compound.

In one embodiment, the compound is an antibody or antibody fragment.

In some cases, evaluating the response includes detecting covalent or non-covalent binding of the compound to the target cell.

In an exemplary embodiment, the method is a cytometry method.

In yet another general aspect, a method is provided. The method, according to one embodiment, includes providing a liquid having therein a plurality of particulates, the particulates being substantially sequentially ordered in a streamline of the liquid, the liquid being externally controllable to provide flow in a first direction and a second, opposite direction, measuring a target particulate from the plurality of particulates at or near a measurement area while flowing in the first flow direction, flowing the liquid in the second direction and measuring the target particulate at or near the measurement area. The sequential order of the particulates remains substantially unchanged during flow in the first and the second flow directions during measurement. The target particulate is repeatedly measured by iterating a process of measuring the target particulate in a first flow direction, reversing the flow direction, and measuring the target particulate in an opposite direction to the first flow direction. The target particulate is a cell, and the measurement area is a focal point or plane of a laser or camera. The measurement includes measuring light scattered light from the target particulate or capturing a photographic image of the target particulate. One or more of the particulates is labeled with a fluorescent tag. Measuring includes providing a light beam with a propagation axis orthogonal to a flow axis of the liquid. The method further includes providing a detector adapted to receive measurement signals, and detecting the measurement signals resulting from interaction between the light beam and the target particulate or a moiety attached to the surface of the target particulate. The light beam is output from a laser, the detector is a charge-coupled device or array or a camera, and the measurement signals includes one or all of attenuation, wavelength shift, collimation, or mode structure. The liquid is contained within a capillary adapted to provide fluid flow, where the capillary is between 0.010 mm and 1.0 cm in diameter. Being externally controllable to provide flow in the first and the second directions is accomplished by providing a pump, where the pump includes an inlet port and an outlet port, and where the pump is adapted to provide positive or negative pressure to both inlet port and outlet port. The method further includes connecting the inlet port to an input end of a capillary, and the outlet port to an output end of the capillary, and controlling the pump to provide an oscillatory pressure differential between the inlet end and the output end of the capillary, wherein the pump is a positive displacement pump. In this embodiment, the method is a cytometry method.

Advantages of the systems and methods over current flow cytometry technology include the ability to track individual cells, or sets of individual cells, in real time, and extract single-cell growth, division, and partition functions of their physiological states. Further advantages include significantly decreased error in measuring particulate characteristics for large samples, "real-time" monitoring of cellular growth for multiple target species, reduction in the required cell population size to successfully carry out experiments, and improved purity in sorted cell populations, among others.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages will be apparent from the drawings and detailed description, and from the claims.

DETAILED DESCRIPTION OF ILLUSTRATIVE EMBODIMENTS

Figure 1:
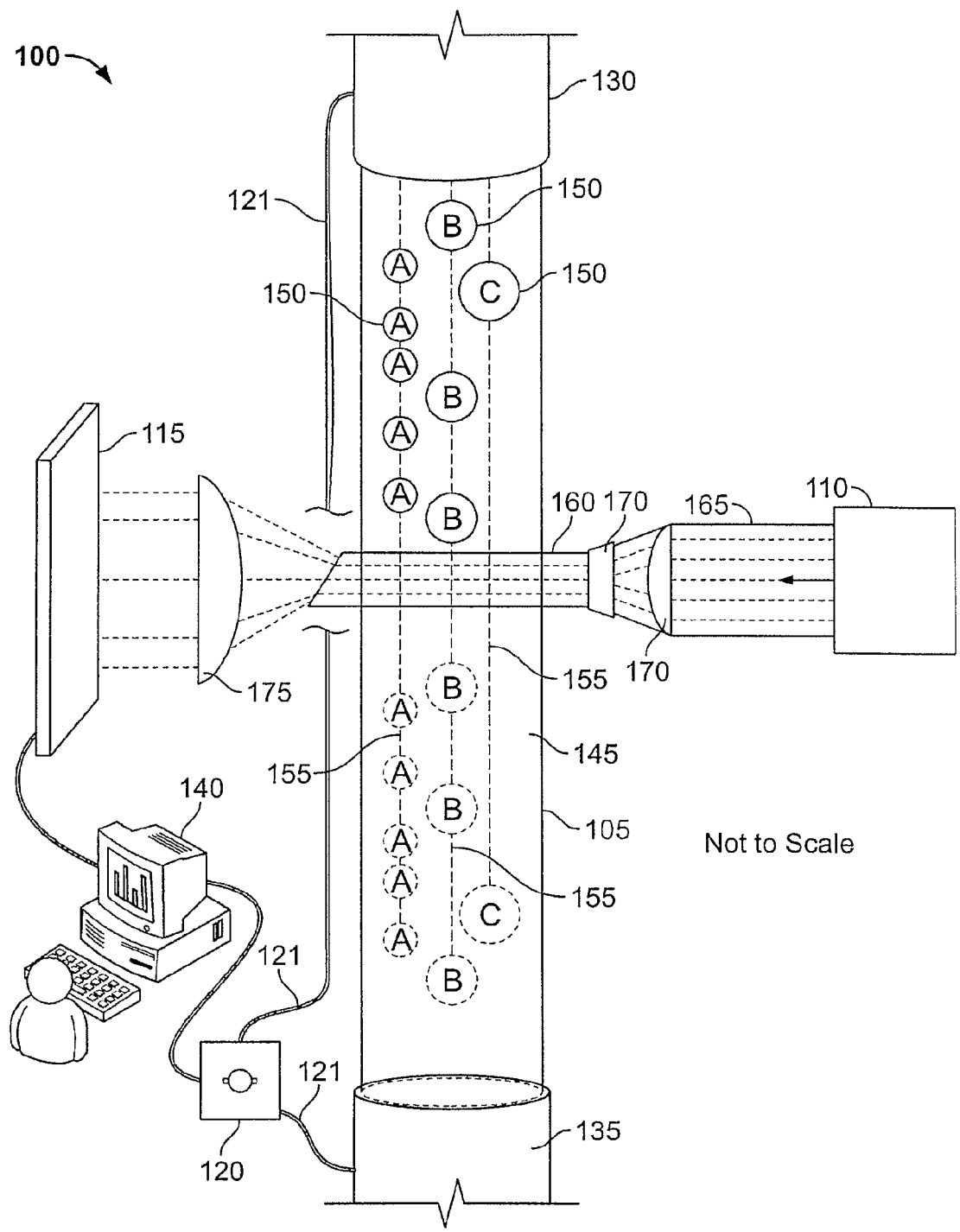
FIG. 1 is a schematic representation of a particulate analyzer (PA), according to one embodiment.

A particulate analyzer (PA) is described. In general, a PA can be an apparatus configured to flow a suspension of particulates in a stream of liquid in two or more directions, and can include equipment configured to analyze the particulates in a certain region of the flow. In one embodiment, a PA can exploit certain behaviors of particulate flow, in particular, the Segre-Silberberg effect described below, a two-phase flow phenomenon that can cause particulates to become ordered in a streamline fluid, where the order of the particulates is maintained regardless of fluid flow direction. In some embodiments, detection equipment can be appropriately positioned near the streamline, allowing measurements of a select particulate or groups of particulates (commonly referred to as a "plug" of particulates).

In general, the PA can record multiple measurements on a single particulate or plug by flowing the particulates through a measurement area in a first direction, reversing the fluid flow direction, and flowing the particulates through the measurement area in a second direction. The order of the particulates within the streamline can be substantially preserved during the oscillating fluid motion. In some implementations, changes in one or more target particulates can be monitored, such as the growth or division of a cell over a period of time.

Segre Silberberg Effect

Dilute particulates suspended in a fluid and subjected to Poiseuille flow can accumulate at an equilibrium radius within a tube that contains them. This phenomenon is known as the Segre Silberberg effect (Segre Silberberg, 1961, 1962). Substantially all particulates of significant particulate-to-tube radius ratio can self-organize on the same streamline within the flow, and therefore can have the same velocity, independent of the direction of flow.

Particulates in a flowing liquid can experience a "lift force," $F_{lift}$, equal to $F_{lift}=k\Omega_S U_S$, where k is a proportionality constant, $\Omega_S$ is the angular slip velocity, defined as the difference between the angular velocity of the particulate and the angular velocity of the particulate at the equilibrium radius, and Us is the translational slip velocity between the particulate and the fluid (Joseph et al., 2002). Numerical solutions to theoretical models suggest that the lift force on a particulate develops in such a way that a particulate on the centerline is pushed toward the wall, while a particulate near the wall is pushed toward the centerline. Thus, a steady-state radial position (i.e., from substantially the center of a cross-section of the fluid within the tube) can generally exist where the forces are equal in opposite directions.

Competing with the lift force are random thermal forces within the flow. The balance between lift and thermal force can determine whether a particulate remains in a particular streamline or crosses to an adjacent streamline within the flow, and hence change its velocity. The probability of finding a particulate within a streamline in a radial direction from the centerline of the flow is expressed by the Fokker Planck equation:

$$u\frac{\partial p}{\partial z} = D\left(\frac{\partial^2 p}{\partial r^2} - \frac{1}{k_B T}\frac{\partial}{\partial r}(F_{lift}(r)p)\right) \quad [1]$$

where u is the average velocity of the flow, z is the distance in the axial direction, D is the diffusion coefficient, r is the distance along the radial direction, and $F_{lift}$ is the lift force on the particulate at a radial location r.

The non-dimensionalized form of the Fokker-Planck equation is written as $$\frac{uR^2}{DL}\frac{\partial p}{\partial z^*} = \frac{\partial^2 p}{\partial \eta^{*}} - \frac{F_{char}R}{k_B T}\frac{\partial}{\partial \eta}(F^*(\eta)p), \quad [2]$$

where $$z^* = \frac{z}{L}, \eta = \frac{r}{R}, \text{ and } F^* = \frac{F}{F_{char}},$$

u is the average velocity of the flow, L is a length scale orthogonal to the radial distance r, R is the tube radius, and $F_{char}$ is a characteristic force scaling with the lift force F(x).

The dimensionless group $$\frac{F_{char}R}{k_B T}$$

is a Peclet number that describes the balance between the thermal fluctuations and the imposed lift force. For large Peclet numbers, i.e., Peclet numbers much greater than one, the system lacks sufficient energy to push the cell against the lift force and thus the particulate cannot cross streamlines. For small Peclet numbers, i.e., Peclet numbers much less than one, the system has sufficient thermal energy to overcome the lift force, and the particulate can cross into other streamlines. Setting $F_{char}$ equal to the force a spherical particulate experiences when attached to the wall, the Peclet number can be expressed as:

$$N_{Peclet} = \frac{150u^2a^4\rho}{k_BRT}, \quad [3]$$

where a is the cell radius, ρ is the density of the fluid, $k_B$ is the Boltzman constant, and T is the absolute temperature (Leighton and Acrivos, 1988).

Cell Population Balance Equations

A cell population is composed of individual cells that each separately contributes to the properties of the entire population. The state of a cell can be quantitatively expressed by a so called physiological state vector that consists of a quantitative representation of the amount of each component that constitutes a cell. Thus, the state of a cell population can be defined by the density function describing how these cellular states are distributed within a cell population. A particular cell type can be thoroughly understood if it is possible to predict how the state of the cell population changes in time in response to environmental conditions. Examples of environmental conditions include, but are not limited to, temperature, pH, salinity, light conditions, exposure to magnetic fields, exposure to a pharmaceutical compound, available oxygen, fermentable and non-fermentable sugars, lipids, polypeptides, or an aqueous chemical compound. Examples of aqueous chemical compounds include, but are not limited to, environmental pollutants, nutrients, drugs (e.g., pharmaceutical compounds), and secretion products. Such understanding can provide a rigorous basis for determining the best conditions for optimum productivity for applied purposes.

The quantitative framework that can provide such description consists typically of population balance equations. These equations can describe the time evolution of the density function reflecting the distribution of states within the cell population. However, one complication is that the parameters of the equation are unknown for most cell systems. In general, the parameters can consist of three fundamental physiological functions: the rate function, the division rate and the partitioning function. The rate function can describe the growth rate or velocity of how the physiological state vector changes in time, and depends on the state of the cells and the cell environment.

The division rate can express the rate that cells divide at a given physiological state, and the partitioning function can describe how cells partition their components at cell division. The experimental determination of these three functions is quite a difficult task as it involves the solution of so called "inverse" problems. In this approach the properties of individual cells reflected in the parameters of the population balance equations are extracted from cell population data typically obtained with flow cytometry or microscopy.

This approach is analogous to the Eulerian reference frame in fluid dynamics in which the entire system is represented by measurements as a snapshot at individual time points. In contrast, in the Lagrangian reference frame individual particulates are tracked in time, affording the description of the properties of the entire cell population as the sum of contributions of the individual components.

FIG. 1 is a schematic representation of a PA 100, according to one embodiment. The PA 100 includes a capillary 105, a light source 110, a light detector 115, a pump system 120 that supplies pressure to capillary ends 130, 135, and a master control device 140 that can control electronic and mechanical aspects of the PA 100. In one particular embodiment, the master control device 140 is a computer, for example, a personal computer. FIG. 1 shows the capillary 105 charged with a fluid 145 containing particulates 150 that are individually labeled A, B, C, . . . etc. Each particulate may be distinguishable by, e.g., size, shape, spectral properties, a label attached to the particulate, or other feature of the particulate, or other moieties attached to the particulate. In one embodiment, particulates can be distinguishable based on a Raman spectrum of the particulate itself, or a Raman spectrum of a label attached to the particulate. In another embodiment, particulates can be distinguishable based on a fluorescence spectrum of the particulate itself, or a fluorescence spectrum of a label attached to the particulate.

In general, capillary 105 is a lumen that supports fluid flow. In some embodiments, capillary 105 is a cylindrical glass tube, for example, a glass capillary with a 100 μm inner diameter. In some cases, such as with commercially-available capillaries, the capillary manufacturing processing includes adding a protective polymer coating that can increase the tensile strength of the capillary. This coating can be removed from the measurement area of the capillary 105, for example, by burning part of the polymer coating away with a butane flame.

The dimensions of the capillary 105 can be selected according to design considerations of the PA and other factors. For example, the inner diameter can be selected so as to achieve a high particulate diameter to inner-diameter ratio, which may, in some circumstances, maximize the Segre-Silberberg effect.

In general, it can be desirable to select a capillary with an inner diameter so as not to affect pressure at the pump head, i.e., that the pressure drop over the length of the capillary is less than the maximum pressure that the pump can deliver. In a preferred embodiment, a 100 μm inner diameter provides good compromise between magnitude of the induced Segre-Silberberg effect, pressure drop, and uniformity of beam profile. Uniformity of the laser intensity across the capillary 105 can be important for obtaining position independent signal intensities from particulates. The length of the capillary can be selected by considering the pressure at the pump head. In a preferred embodiment, the capillary length is 75 cm. This length is close to the pressure limit of suitable pump systems and supports a plug of ordered cells of approximately 25 cm.

In general, particulates 150 in capillary 105 can be ordered by moving the fluid 145 in a back-and-forth motion (oscillating the fluid) for an appropriate number of cycles or period of time. In some embodiments, the number of cycles can be 5 cycles, 10 cycles, 100 cycles, or 1000 cycles, for example. In some cases, particulates can become ordered during a single cycle of back-and-forth fluid motion. The back-and-forth motion of the fluid 145 can, as explained above, induce the particulates to organize into discrete streamlines 155 within the fluid 145 according to the Segre-Silberberg effect.

Generally, the fluid can be made to move in an oscillatory fashion by applying appropriate pressures to the capillary ends 130, 135 via the pump system 120. In some embodiments, "pressure" is meant to include both positive and negative pressure. A suitable pump system 120 may include, for example, a positive displacement pump with pump inlet and outlet sides attached to capillary ends 130 and 135 via pressure hoses 121 respectively. In some embodiments, the pump is a Global FIA MilliGAT™ pump (Fox Island, Wash.). In some embodiments, the pump system 120 may comprise a static pressure source applied to the capillary 105, and fluid motion can be achieved by opening and closing vents attached to the ends 130, 135 of the capillary (not shown in FIG. 1). Opening and closing a vent can allow pressure to escape the capillary on one side, and induces fluid motion toward the lower pressure.

In some embodiments, the pump system 120 can be controlled manually. In other embodiments, the pump system 120 can be controlled by the control system 140 as part of an integrated package that automates both fluid 145 movement and the functions of the light source 110 and detector 115 systems, which are described below. Such a package may be embodied in, for example, a software program running on the control system 140.

In general, a "measurement area" 160 is an area where characterization of particulates 150 occurs. In one embodiment, the measurement area 160 is an area substantially equal to the cross-section of the fluid 145 within the capillary 105. In some embodiments, the measurement area 160 may focus on a particular area of the fluid 145 and not include the entire cross-sectional area. For example, the measurement area 160 may focus on one specific streamline within the fluid 145. In such an embodiment, only the particulates 150 within the specific streamline may be characterized.

In general, the measurement area 160 can be a focal plane formed from the output of a light source 110. In one embodiment, the light source 110 is a laser that forms a laser light beam 165 as shown in FIG. 1. In general, one or more optical elements 170, 175 can be used to control parameters of the measurement area 160 such as the field size and shape. In general, optical elements 170, 175 can focus the light beam 165 to a plane 160 as shown in FIG. 1, or, alternatively, to a point within the capillary 105 or streamline 155 (not indicated in FIG. 1). Optical elements 175 can be positioned on opposite sides or at an angle to the side where light enters the capillary 105, and can direct scattered light or image the measurement area 160 onto the detector 115. For simplicity, two optics 170, 175 are illustrated in FIG. 1. It should be understood, however, that multiple optical components can be used to achieve the desired measurement area parameters necessary for a given experiment. Likewise, multiple light sources 110 can be used to interrogate the fluid 145 and the particulates 150 contained within the capillary 105. In one embodiment, a uniform laser beam profile can be created by incorporating a beam homogenizer unit into the optical elements 170. A beam homogenizer can produce a uniform intensity, rectangular shaped beam using a series of beam expanders and collimators.

Generally, detector 115 can be a device for collecting light energy and converting it into electrical signals that can be processed by the control system 140. In some embodiments, detector 115 can be a photodiode, charge-coupled device, or other similar type of light detector. In some embodiments the detector 115 can be a camera that can collect video or still-frame images of the measurement area 160. In this situation, light source 110 can provide "white" light, and optics 170, 175 may include microscope objectives configured to image the measurement area 160 to the camera lens. In some embodiments, light source 110 can emit a narrow band of wavelengths, for example, similar to the output of a diode laser, to interrogate certain spectral features of a particulate, or to excite a label having an optical absorption in the range of the wavelength band. In still other embodiments, multiple detectors 115 (with associated collection optics 175) can surround, or be positioned so as to capture scattered radiation from the measurement area 160 off-axis from the beam 165 propagation axis. For example, detectors 115 can be placed behind, and/or on the sides of the capillary 105. The detector 115 can be adapted to collect fluorescence from molecules or inorganic clusters used as labels on the particulates, such as fluorescent nanocrystals and the like.

In general, particulate measurement and detection is not restricted to using optical, i.e., electromagnetic-based modalities. In some embodiments of a PA, acoustic generators and detectors can be used to detect particulates 150 as they pass through the measurement area 160. Such embodiments include, but are not limited to, radio frequency (RF), harmonic, and ultrasonic devices, as known and recognized by those skilled in the art of cytometry.

In general, the detection of particulates can include detecting fluorescence from particulates labeled with a fluorescent moiety, identifying light scattering patterns on a CCD device 115, and any other detection method that is generally applicable to cytometry.

In general, a PA can include components that allow for signal detection distal from the measurement area 160. In one implementation, referring to FIG. 1A, a waveguide-PA 175 includes a capillary-waveguide 180. Capillary-waveguide 180 can be any suitable lumen that allows scattered light from particulates to be "channeled" in a direction along the capillary-waveguide 180. Exemplary capillary-waveguide 180 materials include fluorine-containing polymers, including amorphous fluoropolymers, such as Teflon® AF, sold by DuPont.

A capillary-waveguide 180 constructed from Teflon® AF has the unique optical property that the refractive index of the polymer is lower than water. Thus, a water-filled Teflon AF capillary-waveguide (e.g., those sold by Random Technologies Inc. (San Francisco, Calif.) behaves as a liquid core waveguide and functions as a fiber optic. Furthermore, the material itself is substantially transparent to both UV and visible light. Thus, a laser can be shined perpendicular to the axis of the capillary-waveguide 180, and, as individual cells flow through the measurement area 188, the orthogonally scattered light can be collected in approximately a 30° cone and guided to a distal end of the capillary-waveguide.

The waveguide-PA 175 includes a pump system 185 with associated tubing 185a, 185b that can circulate fluid in a circuit that includes the pump 185, tubing 185a, 185b, connector tees 187a, 187b, and the capillary-waveguide 180. In one implementation, fluid is pumped from the pump 185, through tubing 187a to a connector tee 187a. Connector tees 187a and 187b are configured to flow fluid through them, and are transparent enough to allow light from the capillary-waveguide 180 to propagate through them. An exemplary tee ("coupler," part number P-713) is available from Upchurch Scientific, Oak Harbor, Wash. Fluid continues from the connector tee 187a into the capillary-waveguide 180 and travels toward the distal end (i.e., toward connector tee 187b). Particulates can pass through the measurement area 188 and scatter light when they encounter the light field. Scattered light can be internally-reflected as is known in the art of waveguides. The fluid may continue toward the distal end of the waveguide 180, and, upon reaching connector tee 187b, flow through tubing 185a back to the pump 185 where it can continue to circulate.

Figure 1A:
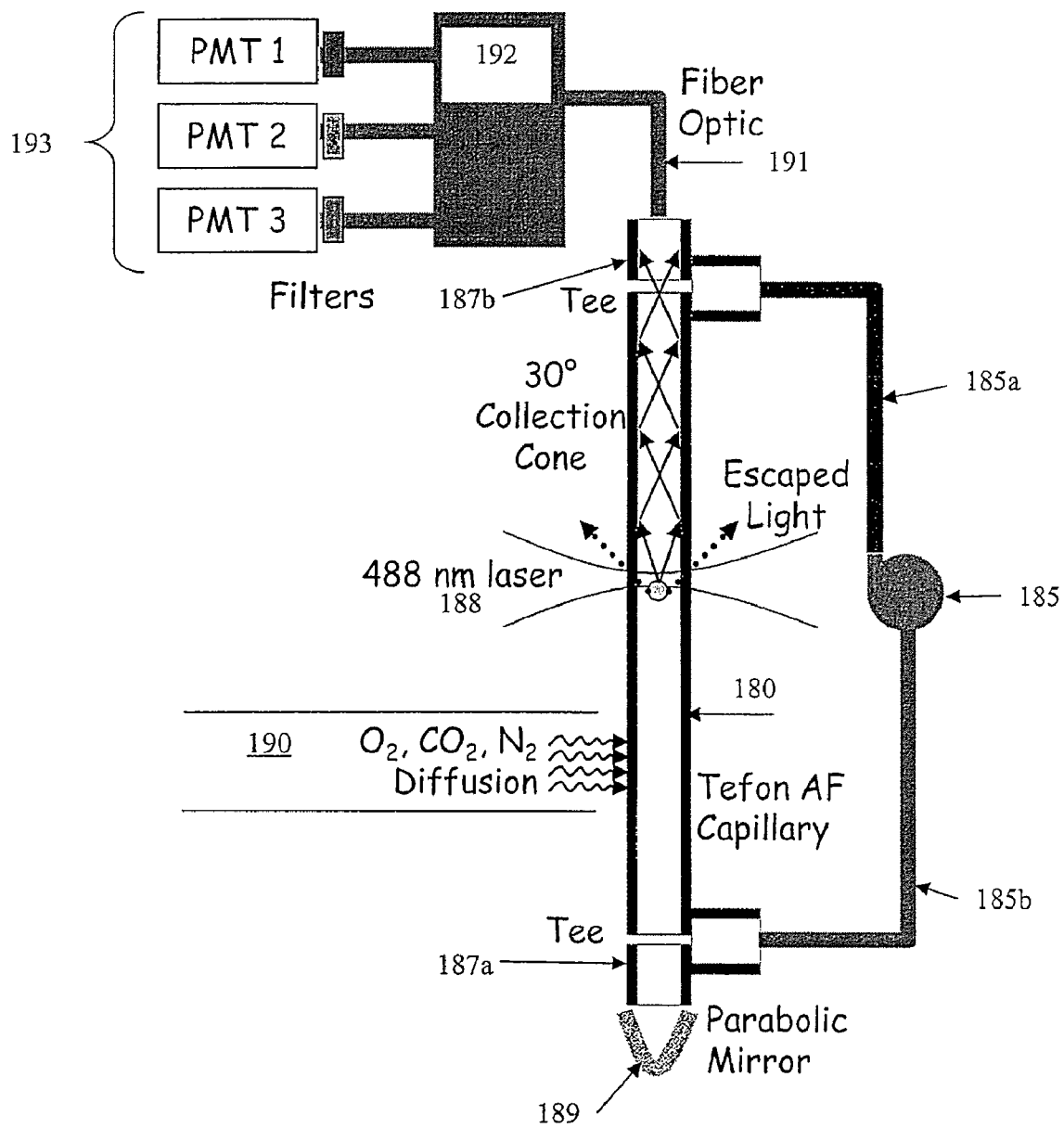
FIG. 1A is one embodiment of a PA that includes a capillary-waveguide.

Light that is scattered from a particulate in or near the measurement area 188 can undergo internal reflection and can be directed by the capillary-waveguide 180 toward the end portions. The connector tees 187a, 187b act as couplers to allow light to propagate out of the waveguide 180 and into another object. In some implementations, a detector can be placed immediately adjacent to a connector tee to capture as much light as possible (not shown in FIG. 1A). In other implementations, additional waveguides, such as a solid-core fiber optic waveguide 191 may be coupled to the connector tee 187a, allowing light to be directed to other optical- or electro-optical components. FIG. 1A shows fiber optic 191 directing light to optical components 192 that can separate light according to wavelength, allowing greater versatility in spectral analysis of particulates. A series of photomultiplier tubes 193 can detect selected wavelengths as described above.

One embodiment of optical components 192 includes the use of fiber optic splitters (such as those supplied by Fiber Optic Network Technology Co. (Surrey, British Columbia, Canada), which can reduce the number of required optical elements. These splitters can filter out individual wavelengths of light from the fiber optic 191, and feed the light into a separate PMT 193. The use of a fiber optic splitter may require dividing the signal by the total numbers of installed splitters. The total amount of light collected from each cell can be doubled by installing a mirror 189, such as a parabolic mirror, on one end of the waveguide-capillary to reflect light scattered in an opposite direction to the detector back to the fiber optic collector. As an additional option, fiber optics can be connected to both ends of the capillary and split accordingly.

In general, the waveguide-PA 175 can reduce the number of optical elements and optical alignment required in other PA implementations.

Some of the operational aspects of a PA are described next. In general, referring back to FIG. 1, a fluid sample 145 containing randomly-dispersed particulates 150 can be introduced into a capillary as described above. Particulates 150 above the measurement area 160 (solid circles) can move along their respective streamlines 155 to a point downstream (dashed circles), when the applied pressure at capillary end 130 is greater than that at end 135. Oscillatory motion of the fluid can substantially order the particulates 150 after a certain number of cycles of back-and-forth motion according to the Segre Silberberg effect described above. Afterwards, the particulates 150 should retain their intra-, and inter-streamline position relative to other particulates. It should be understood that ordering the particulates 150 into respective streamlines 155 can be accomplished at or near the measurement area 160, or at other locations within the capillary 105.

The particulate plug, i.e., the group of particulates 150 can be controlled by the control system 140 so as to move the plug through the measurement area 160 where they can be individually measured by the detection system (e.g., detection system 115).

Referring to the particulates 150 illustrated in FIG. 1, with flow in the downward direction, a "B" particulate would be measured first, followed by two "A" particulates, then a "B" particulate and so on. The PA system 100 can perform a repeat measurement of the particulate by reversing the flow direction. The measurement can then proceed with flow in the "up" direction, as particulates cross the measurement area in the order B, A, A, B. The back-and-forth motion of the particulate plug can continue indefinitely and maintain the relative order of the particulates 150. In this manner, the PA can be used to perform multiple measurements on individual target particulates or plugs of particulates 150.

In general, in some situations it may not be desirable (or necessary) to measure the entire plug as in the preceding discussion. In fact, in some cases, it may be advantageous to repeatedly measure only one selected particulate out of a plug of particulates. A pump system 120 with adequate flow control may be able to move minute volumes of liquid within the capillary, and thus effect very small positional changes of a selected particulate. Thus, referring again to FIG. 1, one of the "A" particulates from the B-A-A-B plug may be "singled out" and repeatedly analyzed by oscillating the "A" particulate across the measurement area 160.

Figure 2:
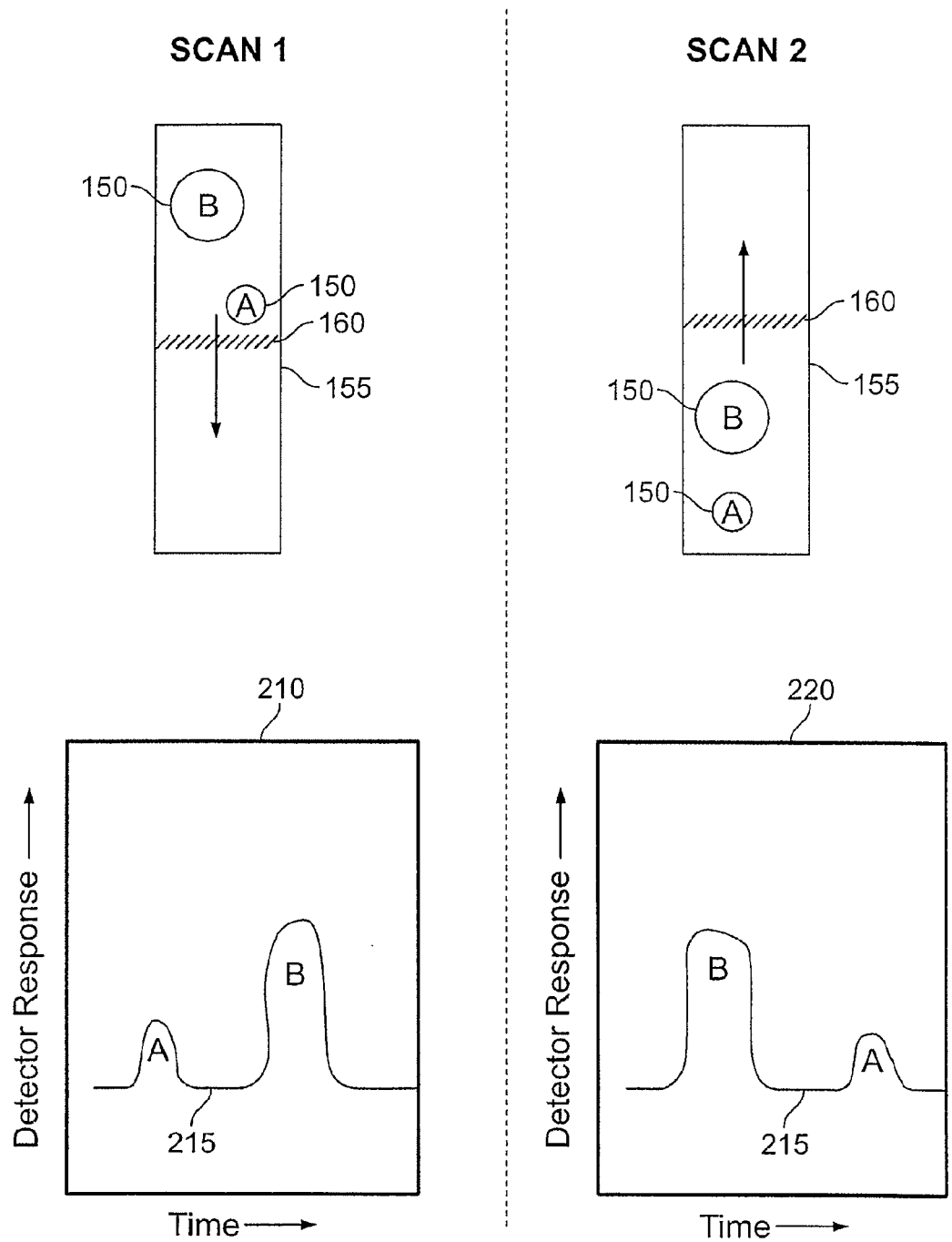
FIG. 2 shows simplified components of a PA according to one embodiment and graphs of detector response vs. time.

FIG. 2 shows simplified components of the PA system 100 and corresponding illustrative graphs of detector response vs. time. The left side of FIG. 2 ("scan 1") shows particulates "A" and "B" within a streamline 155, which itself is contained within a capillary (not shown in FIG. 2). Other components have been omitted for simplicity of the figure. An illustrative chart 210 of detector response vs. time is shown in the lower portion for scan 1, where the line 215 represents data points for the scan. As the particulates 150 move through the measurement area 160 for the flow direction indicated, the detector response can be measured. In this example, the response is of lesser magnitude for particulate A than for particulate B; this may be caused, for example, if particulate A is smaller than particulate B. When the flow direction is reversed, as depicted in scan 2, the detector response is larger for particulate B than particulate A.

A particulate 150 can move into a single streamline 155, and, in some cases, the particulate 150 can diffuse in a direction substantially perpendicular to the flow direction. The position of particulate A in FIG. 2, scan 2, for example, has changed due to axial movement from its original position during scan 1. Diffusion in a direction other than the flow direction can be significant if the detection apparatus is inhomogeneous in its detection along the axial dimension. Diffusion in the axial direction can be significant if the particulate to particulate distance is small enough such that two particulates can diffuse past one another. In general, particulate diffusion in a PA can be controlled by adjusting the concentration of particulates 150 in the capillary 105. This can have the effect of changing the mean axial distance between particulates in the capillary 105.

The PA system 100 can be used to measure cell population dynamics by monitoring cellular growth of individual cells or sets of individual cells (see, for example, the Experiments section, below). As used herein, "a cell population dynamic" refers to a change in any one or more physiological or morphological characteristics of a cell, or cells, of a cell population over time. Cell growth, apoptosis or other forms of cell death, and other physiological functions can be studied as a function of the environment by controlling the fluid parameters, i.e., temperature, nutrient levels, oxygen content, or other factors.

In general, the effects of certain chemicals, e.g., pharmaceuticals, on individual cells can be monitored using a PA. In one embodiment, a cell or cell plug can be localized to the region of the measurement area and exposed to one or more drugs. The effects of the drug(s) can be monitored during specific growth states, e.g., positions in the cell cycle, by oscillating the cell or cell plug through the measurement area over a period of time and measuring appropriate aspects of the cells under the influence of the drugs.

In an exemplary embodiment, a pharmaceutical study can be undertaken by adding a chemical compound to a fluid containing a suspension of cells. The cells can be substantially homogenous with regard to cell strain, lifetime, size, and other parameters, or, the cells can be a mix of several different strains. The PA allows monitoring the effect of a compound on individual cells, and comparison of the effect in one or more cells relative to other cells. For example, referring to FIG. 1, the effect of a compound within the fluid on an "A" cell can be compared to the effect on a "B" cell, and likewise for a "C" cell. The measurement can be repeated as many times as practical by oscillating the fluid back and forth across the measurement area, as described above.

In another embodiment, a PA can be used to recognize cell antibody/antigen binding for multiple combinations of antibodies/antigens within a fluid. For example, a cell culture can be prepared with several different antibodies attached, or potentially attached, to the surfaces of the cells. The PA can monitor antigen/antibody binding using fluorescence methods that are well known in the art, for example, by using fluorescently labeled antibodies and/or antigens. Cells with labeled antibody/antigen complexes that pass through the measurement area can be distinguished from unlabeled cells with a high degree of accuracy, and can be monitored throughout a particular portion of the cell life cycle.

Figure 2A:
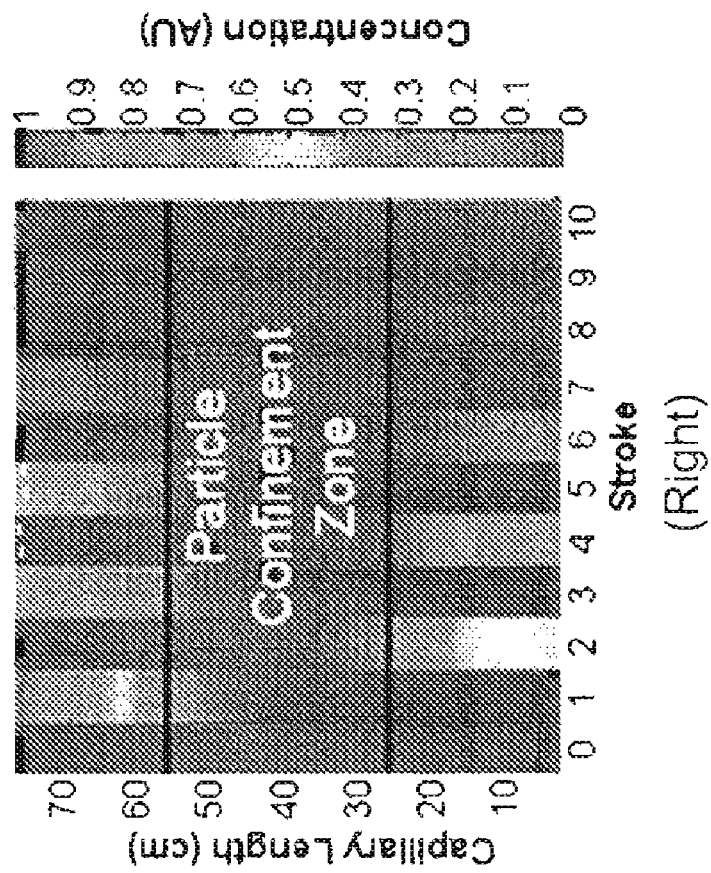
FIG. 2A (Left) is an illustrative embodiment of a pumping system for introducing new fluid into a capillary while maintaining cell order. (Right) Simulation showing a solute concentration at the end of each pump stroke, according to one embodiment.
Figure 2A:
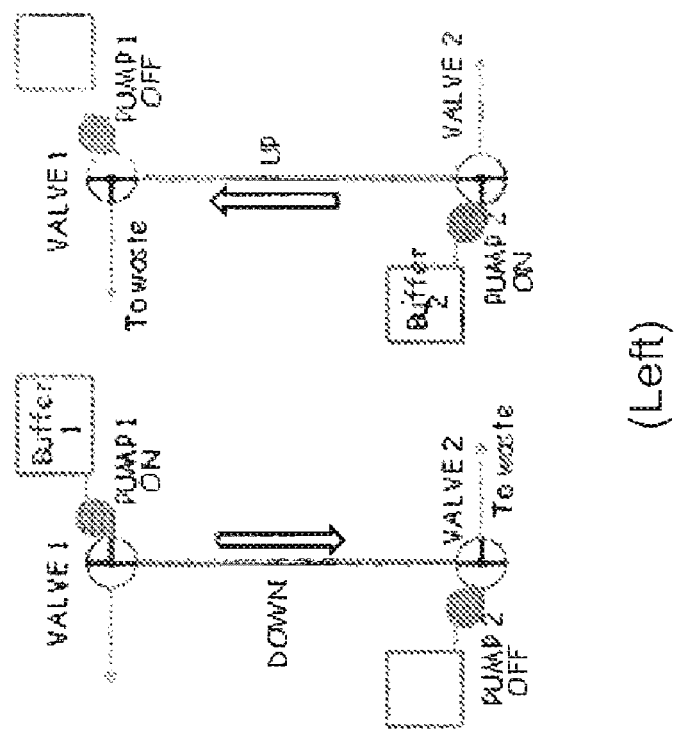

One implementation of a PA includes the ability to replace extracellular fluid as the PA is operating, and without disturbing measurements that may be in progress. Referring to FIG. 2A, left, each end of the capillary can include a valve and pump system. When pumping in the "down" direction, as illustrated, the bottom valve can be actuated and direct fluid to a waste receptacle, while the top valve can be actuated to the pump side. The pump can then be turned on, allowing the fluid to move in the down direction. Similarly, to pump in the "up" direction, the top valve can be actuated to direct the fluid to a waste receptacle, while the bottom valve can be actuated to the pump side. In this manner, a constant supply of fresh medium can be continually introduced to the capillary during each pump stroke.

The right side of FIG. 2A shows a simulation of solute concentration at the end of each stroke, according to the preceding PA implementation. Stroke zero corresponds to the initial conditions. Particulates are retained in the capillary while the fluid is replaced, because the cells can move slower than the maximum velocity of the fluid. Thus, if the tip of the fresh fluid reaches the end of the capillary, then the cells can remain in the capillary.

In general, for a wide range of sizes, the particulates can be confined to a range of potential radial positions approximately 55-75% of the distance from the centerline to the wall. The particulates can thus move at a slower velocity than the tip of the parabolic velocity profile of the fluid and the particulates may lag behind the tip of the fluid. If the stroke volume is set to where the tip of the velocity profile of the fresh fluid reaches the end of the capillary, then the particulates may be retained in the capillary. In this situation, the capillary can be modeled as a laminar flow reactor with dispersion, referred to as Aris-Taylor dispersion. This can be simulated by continually introducing fresh medium at the inlet of each stroke during the oscillation. Thus, as shown in FIG. 2A (right), given a capillary initially devoid of a solute, the oscillatory flow scheme can replace 99% of the contents of the capillary within 10 strokes, while confining the particulates in the capillary. This approach can reduce the required volume of fluid in the system from 20 mL to less than 100 μL.

In general, if the capillary is formed of a gas-permeable material such as a perfluoro polymer, gas concentrations within the fluid can be controlled by adjusting the gas mix flowed over the capillary. Teflon AF, for example, has a large gas permeability. In one implementation, anaerobic conditions can be obtained in the fluid by flowing a non-oxygen gas over the waveguide, for example, by blowing the nitrogen gas from a gas tube 190 over the capillary 180. In another implementation, carbon dioxide can be blown across the waveguide to adjust the pH of the fluid in the capillary.

In general, the temperature of the capillary (e.g., capillaries 105 and 180) can be controlled by known methods. In one implementation, warm or cool gases can be blown over the capillary using, e.g., gas tube 190. In another implementation, the capillary can be fitted with a thermally-conducting jacket that can be heated or cooled. In such an implementation, a section of the capillary may remain open so as to allow line-of-sight to and from detection systems and light sources.

In yet another implementation, the flow circuit of the fluid can contain a thermal bath that is heated or cooled to a desired temperature.

In one general aspect, a PA system can be configured to sort particulates. The sorting mechanism can include an integrated flow switch that alters the path of a detected particulate according to the measurement results. For example, a flow switch can be activated that alters the path of a cell after it has been measured such that large cells flow in one direction and smaller cells flow in a different direction. If there is any ambiguity in a given particulate signal, the fluid can be backed up such that the particulate passes through the measurement area again. A second, third, and even fourth measurement of the particulate can then take place to more accurately measure its size.

Figure 3:
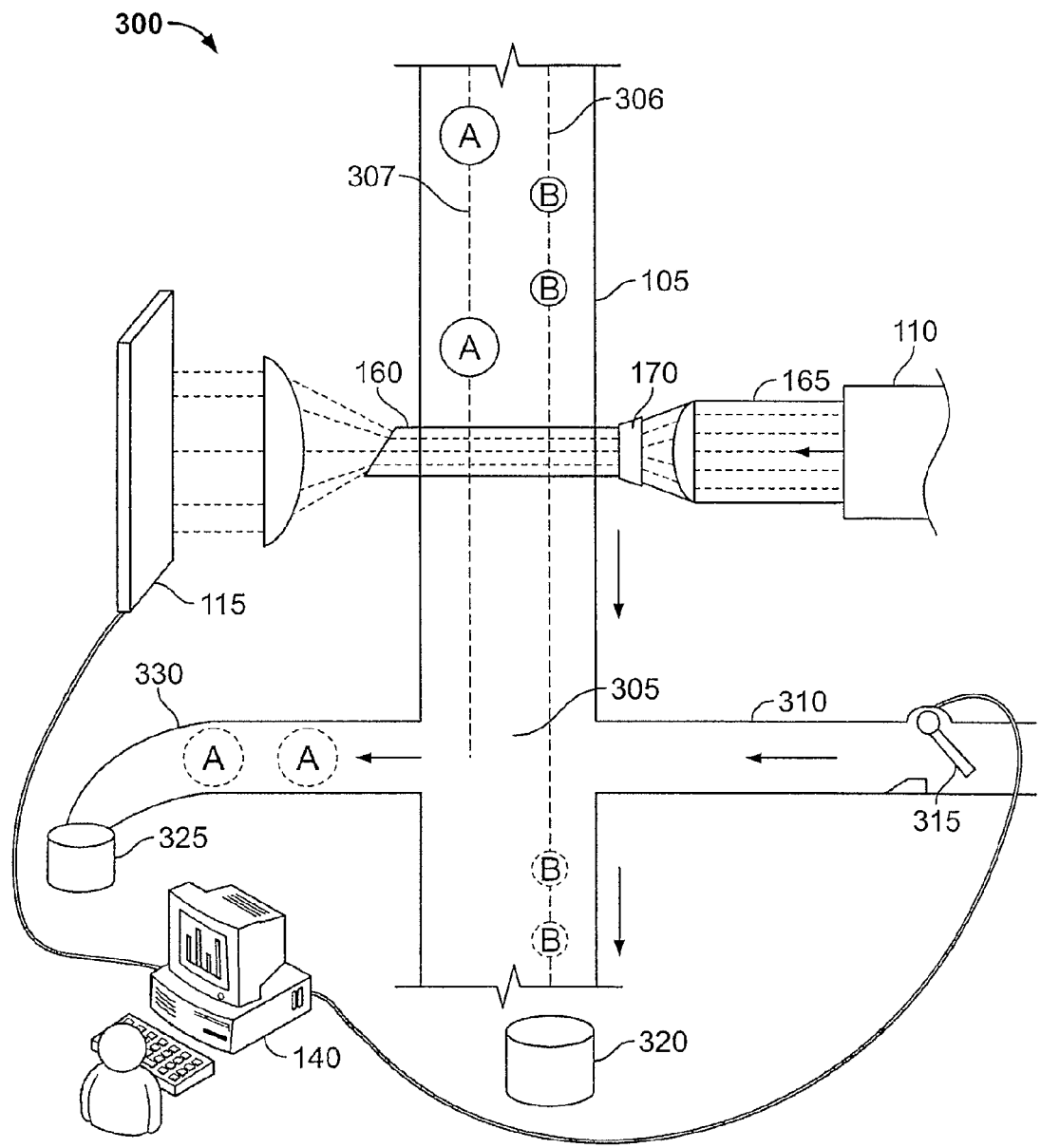
FIG. 3 is a schematic representation of a sorting-PA, according to one embodiment.

FIG. 3 is a simplified schematic representation of a sorting-PA 300 according to one embodiment. In this case, the sorting-PA 300 can be used in a particulate tracking and sorting mode. In some implementations, the sorting-PA 300 can include the elements of the PA system 100 shown in FIG. 1. Not all elements of FIG. 1 are shown in FIG. 3 for clarity. The sorting-PA 300 includes a capillary 305, a measurement area 360, a detection system 315, and optical components 370 to carry out the desired measurement technique. The capillary 305 can have a cross-flow portion, or intersection, generally indicated at 306, which can re-route cells from their downward path onto a different path, in this embodiment, to a tube 330. Tube 310 can be used to apply fluid into the capillary 305 at intersection 306. The application of fluid pressure from tube 310 can be controlled by the control system 340 so as to start flow at an appropriate time, for example, the amount of time it would take a particulate to travel a distance from the measurement area 360 to the intersection 306, taking into account the speed of the fluid, and after receiving a signal from the detector 315.

For example, referring to FIG. 3, the "A" and "B" cells on streamline 307 and 306 respectively can be detected as they pass through the measurement area 360. After a calculated time delay, the control system 340 can apply fluid pressure to tube 310 via a flow switch 315 when an "A" cell is detected. The calculated time delay can correspond to the travel time of the "A" particulate from the measurement area 360 to the intersection 306. Substantially all "A" within a larger population of cells (i.e., a population that may include B, C, and D cells, for example) can be deflected to tube 330 and collected in a repository 325, while the B cells (and others, if present) continue along their streamline path 306 and collected in a separate repository 320. Detection of "A" cells in this example can be achieved, for example, by focusing the light beam 365 to a point on streamline 307. The "A" cells, alternatively, may be labeled with a marker that is detectable by passing through a focus plane 360 as has been described.

In all embodiments, a sorting-PA system may include multiple intersections and sorting modalities that allow virtually unlimited sorting capability.

In one embodiment of a sorting-PA, particulates can be sorted based on particulate history. Sorting based on particulate history can enable selection of particulates such as cells with a particular history (such as growth or division) and not based solely on a property at a discrete point in time.

One implementation of such an embodiment includes using a low-angle "Y" valve positioned on the fluid path, distal to the area where the cells are oscillated within the capillary. When sorting is desired, the Y valve can be actuated, and a plug of particulates can be pumped into a sorting capillary. In this implementation, the flow rate of the liquid can be measured, allowing computation of the velocity of each particulate by two different methods: 1) comparing the forward scattering peak width to the peak height to extract the velocity; or 2) timing the velocity of a particulate, for example, by using two laser beams positioned axially and at a known distance apart, and measuring the particulate arrival time at each beam. When a particulate crosses a first beam, a timer is started; when the particulate passes the second beam, the timer is stopped. Because the distance between the two beams is known, the particulate velocity can be calculated. With either method the velocity of each particulate can be calculated, making it possible to accurately determine when each particulate will arrive at the Y-valve, which can then be appropriately activated.

One variable that can affect the "purity" of sorted particulates in the sorting-PA is the distance between particulates in the capillary and the flow rate of the system. By adjusting these two parameters, the window of time for sorting a particulate out of a plug can be lengthened, and the probability of isolating a desired particulate is increased. The distance between particulates can be increased by using a narrow capillary before the area where sorting occurs.

In one embodiment, a sorting option allows particulates to be added to, or removed from, a plug of particulates during a cycle or experiment. In this embodiment, and referring to FIG. 3, a plug of cells can be moved toward a sorting intersection 306 by applying pressure to one end of the capillary 305. When a selected particulate reaches the intersection 306, the flow in the main capillary 305 can be stopped, and a switch 315 can be activated to produce cross-flow from tube 310, thus removing only the selected particulate from the plug. The cross-flow can then be stopped. The flow direction within the main capillary 305 can then be reversed, moving the plug back (in this case toward the measurement area 360) so that continued measurements can be performed on the plug, absent the removed particulate.

In a somewhat similar fashion, particulates can be added to a plug during a cycle or experiment. For example, tube 310 may contain a concentration of particulates to be added to a plug. One or more particulates from tube 310 may be added to a plug in the main capillary 305 by moving the plug to the sorting intersection 306, stopping the plug, and initiating cross-flow from tube 310. The cross-flow can introduce one or more particulates into the intersection 306 area, at which time the cross-flow can be stopped, and the plug can be moved back toward the measurement area 360 with one or more added particulates.

In one implementation of the above embodiment, an additional detection system can be placed at or near the intersection 306 (not shown in FIG. 3). The detection system can be any of the detection systems described herein, as well as others. One purpose of the additional detection system is to be able to verify that a selected particulate is indeed within the sorting area (i.e., intersection 306) before activating cross-flow for removing, or adding particulates to or from a plug. Similarly, the detection system can be used to verify that a particulate has been added to a plug before the plug is moved away from the intersection 306. In one embodiment, a laser beam may be focused into intersection 306 at a right angle the capillary 305. A detector, such as an electro-optic detector can be placed on the opposite side of the capillary 305 and can detect fluorescence, scatter, or other signals from the particulates. In another embodiment, a camera can be placed proximal to the intersection 306 to capture images of the particulates as they approach or enter the intersection 306.

In one implementation of the above embodiment, a waveguide-capillary is used. In this implementation, a first light source can be used to create the measurement area, and a second light source can be used to detect particulates when they arrive at the cross-flow intersection, e.g., intersection 306. In some embodiments, the first and second light sources produce different light outputs. For example the first light source may be a laser operating at a first wavelength and the second light source can be a laser operating at a second wavelength. The waveguide capillary can channel scattered light from either (or both) light sources to detection equipment residing outside of the waveguide capillary, as shown, for example, in FIG. 1A. In some cases it may be advantageous to use a beam splitter to separate light from the first and second light sources so that separate detectors can be used to individually detect light from the two sources.

Cell cultures are often used to produce a multitude of useful products ranging from highly valued therapeutic polypeptides, to low cost commodity chemicals such as ethanol. The optimization of cell culture productivity can be a goal in some production process and can be important for economic vitality. In general, according to one embodiment, a PA can be used for counting, sorting, and isolating cells. In some cases, the sorting-PA can yield highly purified cell (and other particulate) populations. In one embodiment of a PA, cells can be characterized and isolated according to desired strains, size, viability, or other distinguishing features.

In any of the above embodiments and implementations, sorting, adding, and removing plugs and particulates can be computer-controlled for maximum efficiency.

In one general aspect, the master control device (e.g., master control device 140 in FIG. 1) of the PA can include computer hardware and software that permits PA particulate tracking, detection, and control. Generally, the software can include executable instructions that control various functional and operational aspects of the PA, including, but not limited to, flow control systems, detection apparatus, light sources, and collection assemblies (for collecting sorted particulates).

For example, one or more software programs operable on, e.g., a personal computer, can control flow oscillation within the capillary, the light source, the detector, and any other devices so as to identify a series of particulates as they pass through a measurement area. In one embodiment, the PA includes a software package that allows the signal detected from an unknown particulate to be compared to a library of known particulate responses, so that a determination of the unknown particulate may be performed. In one such embodiment, the library of known responses may include shapes and/or sizes of known cell morphologies, allowing an unknown cell to be characterized by comparing certain structural features of the unknown cell to the known cell.

Generally, the computer program can keep track of the order of particulates as they pass back and forth through the measurement area 160. A change in the nature of a particulate, for example, a cell that is undergoing growth or division can be tracked by the program. In the case of cell division, a new particulate (e.g., the birth of a daughter cell) can be detected because a new signal can emerge where, in a prior scan, the signal may have been absent. The software program can keep track of each particulate signal as it crosses the measurement area 160 in both forward and reverse flow directions.

PA software can be developed in a visual programming language, such as LabVIEW, available from National Instruments Corporation. An exemplary PA software embodiment can carry out one or more of the following functions. It should be understood that the following functions need not be carried out in the order presented, and, each of the described steps may be iterated more than once. In one embodiment, the software may be stored on a master control device, such as master control device 140 shown in FIG. 1. In another embodiment, the PA software may be stored remotely, such as on a network or remote computing system.

The PA software program can digitize the amplified signal from each photomultiplier tube at a frequency of 100 kHz at a resolution of 16 bit. The program can then detect when an event occurs and store a timestamp and a slit-scan from the particulate. The data acquisition rate can be sufficient to yield 60 data points per event at an event rate of 20 cells per second. The data can be stored in ASCII format and consume about 500 bytes per event. For an expected cell tracking experiment of 300 cells per stroke with light scattering detected over three PMTs at 2 strokes per minute for 3 hours, the total file size per experiment may be approximately 162 MB. This file size can be reduced by storing the data in binary format using a standardized file format as implemented with traditional FCS flow cytometry data files.

Simultaneous with event detection, the flow rate in the system can be acquired at a rate of 12.5 Hz at a resolution of 15 bits over a range of 0-40 µL/min and can be streamed to disk, which over the course of an expected experiment can produce a 2 MB file size. During the course of an experiment the flow rate data for each stroke can be integrated to obtain the total volume pumped. During the run, the software can correct the magnitude of each subsequent stroke for any deviations from ideal oscillatory behavior.

Once the data are acquired, an analysis algorithm can extract single particulate data. The first step of an exemplary algorithm may be to compare the time when each particulate crossed the laser for each adjacent stroke in the same direction. From stroke to stroke, the time that a particulate crosses the laser may fall within a definable window of time, thus providing a first level of classification. Based on the distribution of differences between particulate crossing times and the total length of the stroke, up to 125 particulates may be isolated based on time alone. To further increase the total number of particulates that can be analyzed within an experiment, the fact that light scattering properties of real cell populations vary over a measurable range and that these properties change at a much slower rate than the data acquisition rate of the instrument is used. Thus, if neighboring cells fall within the window of times between two strokes, these cells can be differentiated from each other based on their light scattering properties, which would insignificantly change over the 30 seconds between strokes. The number of cells that can be potentially analyzed, therefore, is the product of the number of time windows and the number of light scattering windows. With an appropriate algorithm, it may be possible to analyze at least hundreds of unique cells in a single experiment, which may yield information on the behavior of the cell population.

Once individual cells are identified from the analysis algorithm, the waveforms of these cells can be analyzed for the peak height, width, and area of the signal. Also, since the individual waveforms are stored, additional parameters such as peak skew, dip index, etc., can be extracted depending on the data of interest. Whatever parameter is extracted from the individual waveforms can be analyzed within the context of the population balance equation. Specifically, the derivative of the property change with respect to time can be the rate change function of the cells.

An oblong cell can also be tracked through time. It is indeed likely that cells can be tracked through at least the initiation of division. Thus, the division rate function can be calculated by recording the properties of the cell at a certain point in time. If the cell can be tracked completely through division, then the properties of the daughter cell and the parent cell can be observed immediately after division, thereby obtaining information on the partitioning function. Furthermore, the derivative of the cumulative volume pumped at the time the particulate crosses the laser with respect to time can be proportional to the density of the particulate. Thus, for each particulate in the system, the single cell density can be computed.

At the completion of the data processing step of the software, the user can be presented with several options for displaying the data. In one embodiment, the user can plot the individual functions of the population balance equation, correlate the time course of the properties of the individual cells for the parameter of interest, and the population data of the system for the means and coefficients of variation. Also, the user can be given simulation options that may use the acquired rate, partitioning, and division functions of the population balance equation, and a user inputted initial property distribution and simulate how the total population of cells will behave in time.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, a data processing apparatus. The tangible program carrier can be a propagated signal, e.g., an artificially generated signal, e.g., a machine-generated electrical, optical, or electromagnetic signal, that is generated to encode information for transmission to suitable receiver apparatus for execution by a computer, or a computer readable medium. The computer readable medium can be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits). The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other.

In one general aspect, a PA can be an analytical tool for collecting data that can be used to determine population balance equations. These equations can provide significant insight into the biological complexity of single-cell organisms at the cell population level, due to high-throughput capacity and capability of measuring specific target cells with respect to the population as a whole. Cell cultures can represent complex distributions of cells that act independently of each other but dependently on the environment. Consequently, it can be possible to mathematically detail, through population balance equations, how a culture will change based on changes in the environment. See, e.g., Fredrickson et al., 1967; Ramkrishna, 2000. The model can be a first order partial integral-differential equation. In one approach, the model can consist of a standard balance equation on a culture within the state space of the physiological composition of cells. The cell number rate of change must be accounted for by cellular flux within the state space, also known as cellular growth or cell division, and the partitioning of the internal composition of the cell during division. This can be expressed as:

$$\frac{\partial n(x,t)}{\partial t} + \nabla \cdot [r(x,t)n(x,t)] = \int_x^\infty (2\Gamma(y,t)P(x,y,t)n(y,t))dy - \Gamma(x,t)n(x,t) \quad [4]$$

where n(x,t) is the cell number, r(x,t) represents the single cell growth rate function, $\Gamma(x,t)$ is the division rate function, and P(x,y,t) represents the probability of partitioning a cell of state y into a cell of state x. This equation represents the idea that the probability distribution change, i.e., $$\frac{\partial n(x,t)}{\partial t},$$

is due to cellular flux in state x, i.e., $\nabla \cdot [r(x,t)n(x,t)]$, or because cells rearrange the distribution through daughter cell birth, i.e., $2\Gamma(y,t)$, or mother cell division, i.e., P(x,y,t)n(y,t).

In one general aspect, a PA can be used to collect data that allows rate functions of population balance equations to be determined. The division rate and partitioning functions of cells can be determined by observing morphological change, for example, which may be one observable that the PA detection system monitors. Oblong cells created by mitosis can still behave in an oscillating fluid according to the Segre-Silberberg effect, and exist along an equilibrium radius, i.e., a streamline. See, e.g., Li et al, 2004.

In some PA embodiments, a photomultiplier can be used as a detector in the PA system, and its response can be considered a convolution of the laser beam intensity profile and the cross-sectional area of the cell. The waveform collected from pre-amplifiers, if present as part of the detection system, can directly reflect the interpretation of cell morphology, if the longitudinal axis is aligned with the flow. Due to the fully developed flow in the capillary, however, cells with a longitudinal axis may not align along their longitudinal axis in the flow stream and may instead rotate. See, e.g., Melamed, 1994.

In some cases, the measurement frequency can be greater than the time-scale of cellular growth, and multiple waveforms of a dividing cell can be collected. In this circumstance, an average waveform can be computed to more accurately reflect the true cell morphology. This approach can enable determination of the division rate function and the partitioning function of the cells because the morphological changes during mitosis and cytokinesis should be observable. See, e.g., Block et al., (1990).

Figure 4:
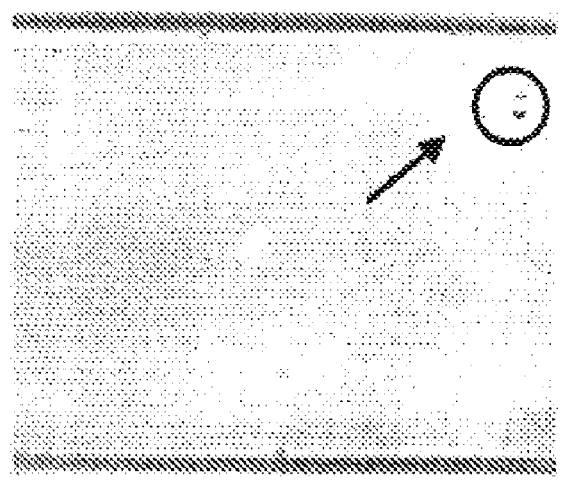
FIG. 4 is a chart depicting the area of a particulate (a yeast cell) vs. time.
Figure 4:
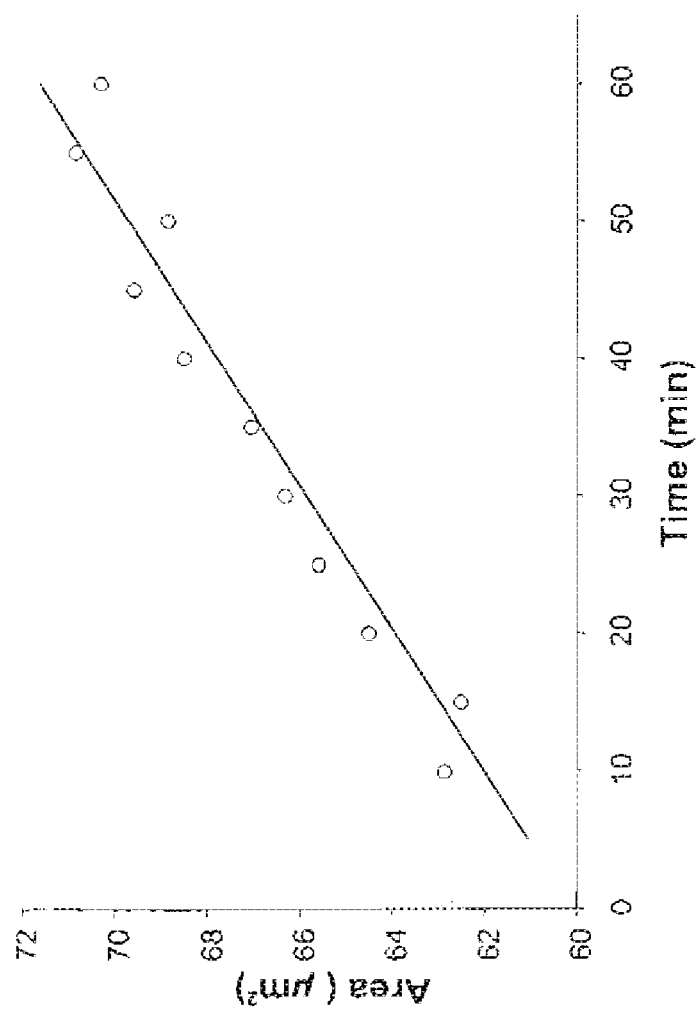

Rate functions of population balance equations can be determined using a PA. In one implementation, a suspension of yeast cells (such as approximately 2 µL, 5×10$^5$ particulates mL$^{-1}$) can be analyzed. The PA can track a number (e.g., 1000) of the cells in the suspension and measure any morphological changes over time. This information can be used to solve the rate functions of the population balance equations described above. In one embodiment, for each cell in a plug of cells, a curve similar to that shown in FIG. 4 can be generated, with a measurement frequency on the order of once every 20 seconds, for example. FIG. 4 shows a plot of cell growth (measured in µm$^2$) vs. time for a selected yeast cell. In one approach, a rate function can be obtained by solving for the derivative of the property of interest with respect to time. In one embodiment, rate functions can be determined according to the methods disclosed in Srienc F, Dien B S., "Kinetics of the cell cycle of *Saccharomyces cerevisiae*," Ann. N.Y. Acad. Sci. 665:59-71 (1992) and Kromenaker S J, Srienc F., "Cell-cycle dependent polypeptide accumulation by producer and non-producer murine hybridoma cell lines: a population analysis," Biotechnol. Bioeng., 38:665-677 (1991).

In one general aspect, a PA can track particulates across streamlines and determine if a particulate moves faster or slower than neighboring particulates. For example, a small cell in one streamline may grow rapidly; when that cell size reaches a point that it no longer remains in its current streamline, it may cross over to another streamline. By tracking the trajectory of the relative distance between cells in that area, i.e., the rearrangement, the cell growth can be monitored.

In some embodiments of a PA, the relative position between particulates can be inferred from the amount of time that lapses between detection of particulates as they pass through the measurement area. In other embodiments, the spacing between particulates can be visually identified, using, for example, photographic techniques that image the measurement area.

In one general aspect, characteristics of the fluid that suspends various particulates, e.g., fluid 145, can be altered during the course of a PA experiment to add or remove constituents, e.g., pharmaceutical products, without disturbing the sequential order of the particulates. In one embodiment the PA capillary can have an injection port through which pharmaceuticals, solutions, or other additions may be added before or during operation of the PA. In other embodiments, the capillary can be connected to a flow switch or reservoir that adds solutions or solids to the fluid 145. The addition of constituents to the fluid may be computer controlled or adapted for manual injection. These embodiments allow the PA system to be used, for example, in series tests for pharmaceuticals where the effect of the pharmaceutical can be studied on a particulate or group of different particulates over time.

In general, the PA fluid can be subjected to any type of stimulus or condition that may affect an aspect of the particulates, and that may be useful in certain experiments. For example, the fluid in the PA capillary can be exposed to certain light, heat, magnetic, radiation, and other conditions. The effect that these and other conditions have on the particulates may be measured by the PA.

Figure 5:
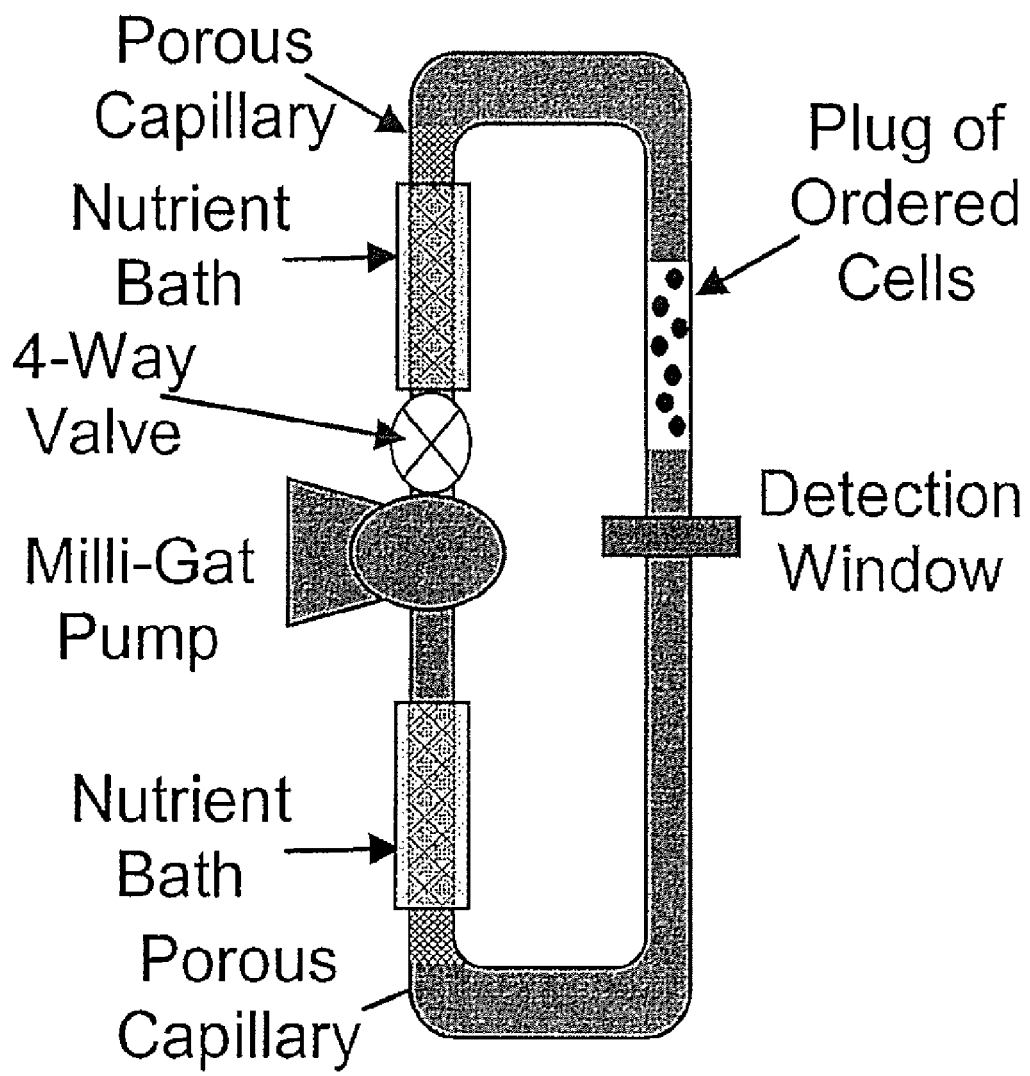
FIG. 5 is one embodiment of a PA that includes a porous capillary.

In general, the PA can include a flow cell that connects on both ends to a porous capillary in order to enable exchange of solute with the interior of the flow cell as shown in FIG. 5.

In one general aspect, a PA can be used to determine the efficiency of mass transfer through the porous regions of a flow cell by comparing cell growth for a set of cells to cell growth conducted in parallel shake flask experiments. For example, a limiting component in the medium can cause cells to reach a stationary state. The kinetics of reaching such state should be the same for cells growing in the capillary as well as for cells growing in a shake flask under the same conditions. An indication that the growth phase can be significantly extended if the growth limiting component is supplied through the porous capillary can be a good test for efficient mass transfer. The experimental test conditions can be evaluated with a model that takes into account mass transfer and growth kinetics. A further test approach can include administering toxic and cell damaging chemicals through the porous membrane. Again the kinetics observed in the capillary can be compared to kinetics obtained from separate batch experiments. Similar experiments can be performed with the diffusive mixing design described above.

Experimental Section

The following experiments, including the methods described to carry out the experiments, and results are considered part of the detailed description and are non-limiting with respect to the claims and the inventive scope of a PA.

Experiment 1. Cell Growth and Single-Cell Tracking

A 7 cm length of 100 µm inner-diameter fused silica capillary tubing was attached using silicon tubing having a 300 µm diameter to a 0.5 µL syringe in a syringe pump. The capillary tubing and syringe pump were mounted vertically. A microscope objective (40× magnification) was placed at a distance approximately equal to its focal length to the capillary. A 340×280 pixel microscope camera was connected to a computer running a custom image processing MATLAB program and pump control algorithm. Next, a suspension of YPH-399a yeast cells in SD minimal medium at a cell concentration of $10^4$ cells mL$^{-1}$ was loaded into the capillary. The control algorithm activated the syringe pump so as to push the fluid in one direction until a cell transited the measurement area. Next, the pump was reversed until the cell transited the image window in the opposite direction. This cycle was repeated at room temperature and an image of the cell was recorded every 5 minutes.

FIG. 4 shows the single cell growth rate r(x,t) extracted from the images by calculating the cell size discretely using image thresholding (1 micron). The camera had a finite exposure time, and hence the velocity of the particulate was kept sufficiently small such that a non-blurred image was acquired. For the system described, the Peclet number was 0.5. Diffusion was therefore significant and the cell was able to reach the capillary wall and adhere to it, preventing further measurements. Despite this limitation, the experiment showed that the same cell in suspension could be analyzed multiple times by reversing the flow direction. A simple control algorithm was sufficient to control the movement of the cell, and nutrient transfer in the capillary was sufficient to maintain cell growth.

Experiment 2. Maintaining Cell Order

This experiment shows that many cells can be observed at the same time. This can be experimentally realized if the order of cells can be maintained over extended periods of time. To experimentally show that the order of a suspension of cells can be maintained during forward and reverse flow, a system was designed where the velocity of the flow was increased such that the Peclet number was on the order of $10^6$. Diffusion in the radial direction, therefore, was expected to be minimal and each particulate was expected to be positioned only along its equilibrium radius.

A precise, repeatable pumping of the fluid can be the most critical aspect of the device. To ensure a precise, repeatable pumping of microliter scale volumes of fluid, a commercially available 'Milli-GAT' pump made by GlobalFIA was used. The 'Milli-GAT' positive displacement continuous syringe pump was capable of bi-directional flow accurate to 10 nL across a wide range of flow rates. The inlet and the outlet port of the pump were connected to either end of the capillary in a closed loop.

A video camera-microscope system could not be used in this case because of the velocity of the particulates. Instead, an Ortho Cytoflurograph 50H flow cytometer was modified to include a 75 cm long 100 µm inner diameter capillary. A capillary of this length can hold 5.9 uL of solution. A laser beam at a wavelength of 632 mm was focused at the midpoint of the capillary. Alternatively, a laser beam at a wavelength of 488 n can be used.

Next, a suspension of particulates was flowed through the capillary. As each particulate transited the laser beam, light was scattered and collected with photomultiplier tubes at two locations: at a small angle <8° from the laser beam axis (forward scatter, which is proportional to particulate size), and orthogonal to the laser beam axis (side scatter, which is proportional to particulate granularity). Different wavelengths of light can be split out of the side scatter signal and the fluorescence of the particulate can be measured. The photomultiplier tube signals of both side and forward scatter were amplified and converted to a voltage signal. The shape of the signal is the convolution of the laser beam intensity and the particle cross sectional area. Subsequently, the forward scatter voltage signal was digitized by a Data Acquisition PCI card at a frequency of 100 KHz, and analyzed by a custom LABVIEW data analysis program in real time.

Figure 8:
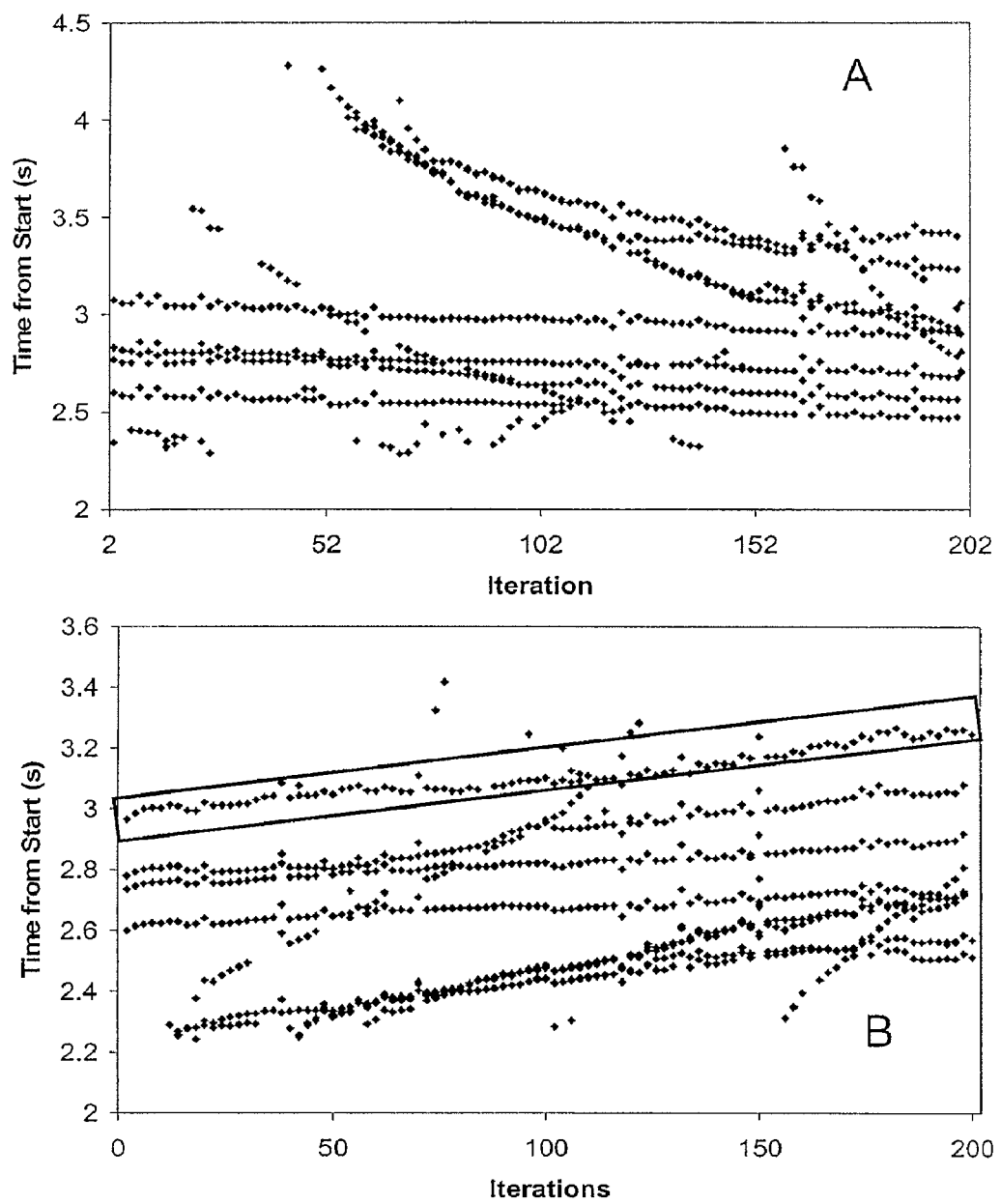
FIG. 8 is a set of two charts plotting detected particulates as a function of time from pump start and iteration.

To test that the relative ordering of particles is maintained over long periods of time, a dilute solution ($10^4$ particles mL$^{-1}$) of 10 μm polystyrene beads in a 1.05 g/L sucrose solution were loaded into the capillary. Next, the Milli-GAT pump oscillated 1 μL of fluid at 2 μL s$^{-1}$ for 202 strokes in 60 minutes. The time each particle crossed the laser relative to when the command to start moving the pump was issued, the peak height, and a slit-scan of each particle were recorded by the custom LABVIEW program. FIG. 8*a* shows a series of ten particles were easily identified over an extended time period. The straight lines in the figure are characteristic of particles that were at the start of the experiment near their equilibrium positions and then stayed in those locations over the course of the experiment. The curved lines indicate particles that were initially positioned far away from their equilibrium positions. During the course of the experiment they migrate to their equilibrium positions. As expected, scans in the 'up' direction are a mirror image of scans in the 'down direction. Furthermore, it is interesting to see that over time, particles cross the detection window earlier in the 'down' direction and later in the 'up' direction. This can be indicative that the polystyrene beads are settling over time due to a density difference between the beads and the carrier solution. Thus, in some implementations, a PA can be used to measure the settling velocity of particles, and thus is able to experimentally determine single cell densities.

Figure 9:
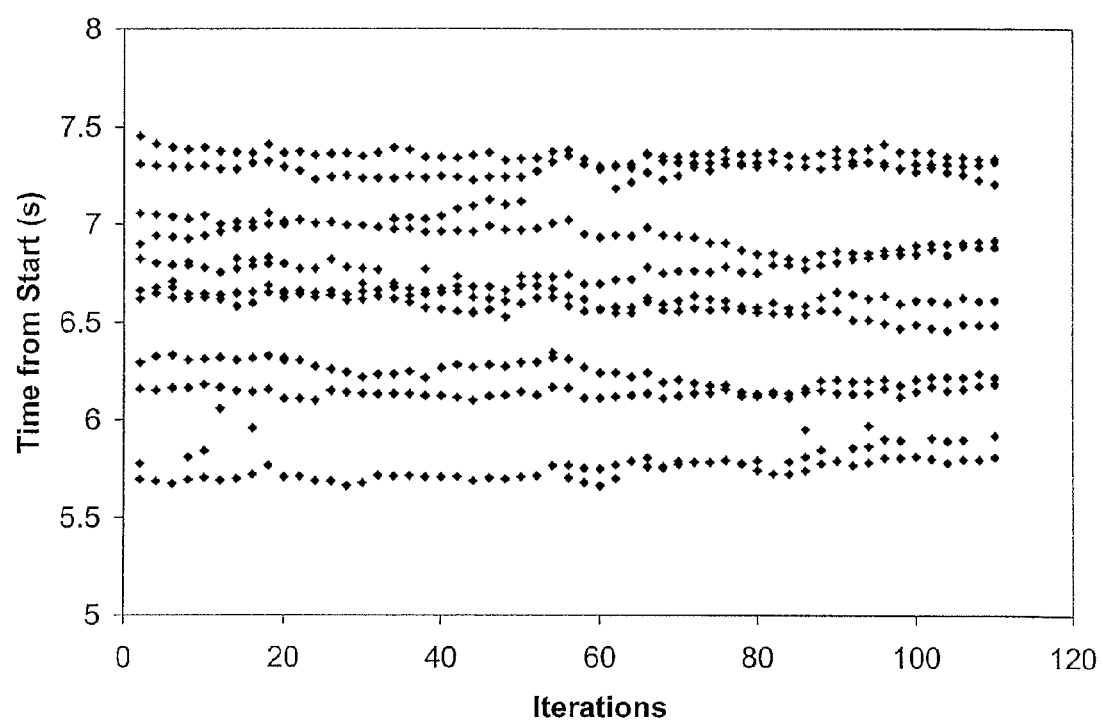
FIG. 9 is a chart plotting detected particulates as a function of time from pump start and iteration.

It is expected that at smaller Peclet numbers, the particles will be able to diffuse over a wider range of radial positions. Thus, particles would be able to cross the interrogation point at different times in a random process. This is observed when the particle Reynolds number is decreased to 0.25 as shown in FIG. 9. In this figure it is important to note that that the time each particle crosses the laser significantly changes over time when compared to the higher Reynolds number flow in FIG. 8.

Figure 10:
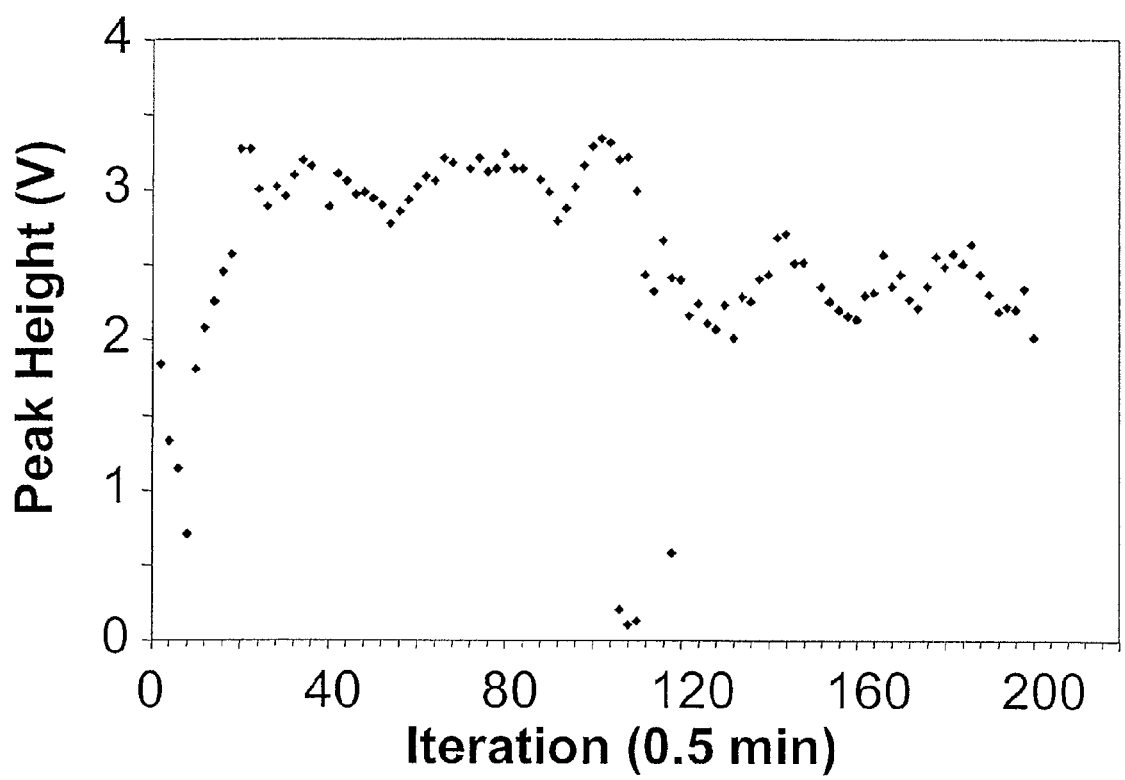
FIG. 10 is a chart plotting peak height vs. iteration for detected particulates.

Since in these experiments, the laser beam intensity in the theta direction is inhomogeneous, repeat measurements of the same particle did not yield identical peak heights as shown in FIG. 10 for the boxed particle shown in FIG. 8B.

Experiment 3. Beam Homogeneity.

The homogeneity of the laser beam can be an important consideration in consistently measuring the light scattering properties of a particulate. In this case, the laser beam was shaped into an ellipse, approximately 120 μm×5 μm. Within the ellipse, the laser beam intensity was Gaussian with a peak intensity occurring at the center of the ellipse. As the laser beam intersects the capillary, the curvature of the capillary compresses the ellipse to a smaller ellipse, approximately 90 μm×5 μm. The inhomogeneous shape of the laser beam intensity can, in some cases, affect the accuracy of the measurements. For example, if two particulates with identical quantities of fluorophores intersect the laser beam at the same location at the same laser intensity, the signal they emit should be identical. On the other hand, if the two particulates intersect at two different locations with two different laser intensities the resulting signals may differ.

This effect is illustrated when an equilibrium radius of particulates intersects a Gaussian laser beam. As the equilibrium radius decreases, the variation in laser beam intensity across the equilibrium radius also decreases. This effect can be experimentally measured by running suspensions of uniform polystyrene microspheres through the device. See, e.g., Shapiro, (1985). For the same flow Reynolds number, larger particulates will have a smaller equilibrium radius than smaller particulates. See, e.g., Matas et al, (2004). The standard deviation of forward scatter signal peak heights can therefore be smaller for larger particulates as shown in FIG. 6, for 3, 6, and 10 μm particulates.

Figure 6:
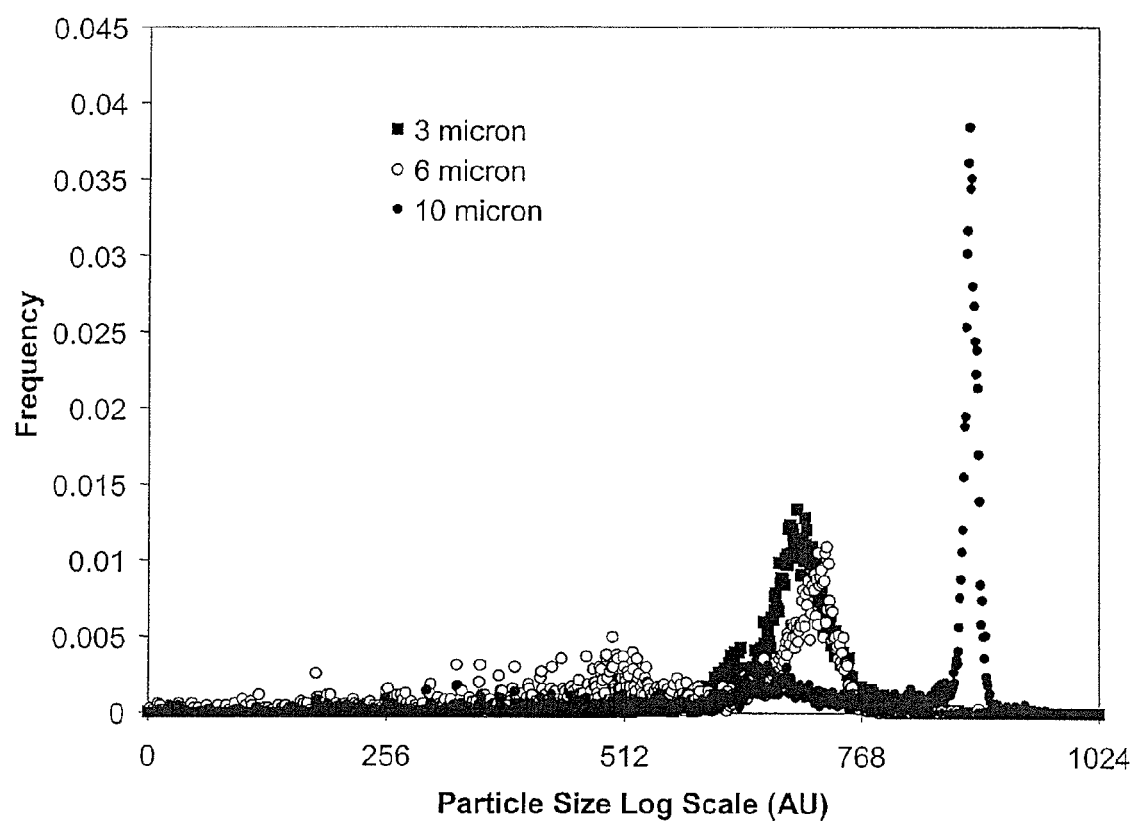
FIG. 6 is a chart depicting frequency vs. particulate size for 3, 6, and 10 micron particulates.

As FIG. 6 shows, despite variation in laser beam intensity, there was sufficient difference in size to differentiate between 3 and 10 μm particulates. To experimentally test that the order of cells in the capillary can be maintained, a mixture of 3 μm and 10 μm particulates was loaded into the capillary. The mixture of particulates in the capillary generated a unique 'barcode' of alternating particulate sizes.

Figure 7:
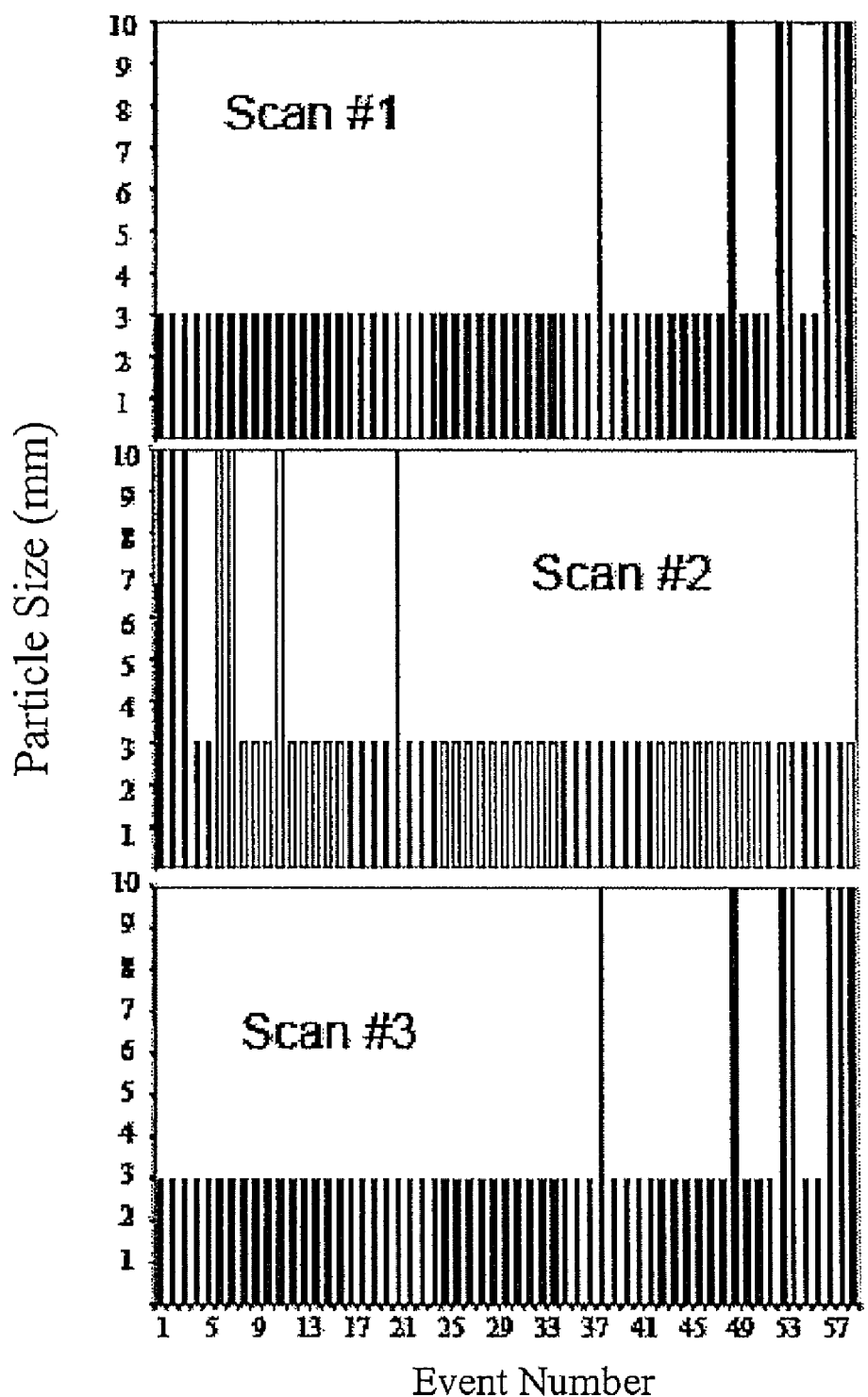
FIG. 7 is a set of three charts depicting particulate size vs. event number.

Next, using the pumping apparatus described above, flow was initiated in the forward direction for 3 seconds at 5 psig, and then reversed for 3 seconds at 5 psig. This process was continued for approximately 50 scans. As shown in FIG. 7, a unique barcode of 59 particulates was preserved for three scans. As expected, the order is reversed for a scan occurring in the opposite direction.

To test that the relative ordering of particulates is maintained over long periods of time, a dilute solution ($10^4$ particulates mL$^{-1}$) of 10 μm polystyrene beads in a 1.05 g/L sucrose solution were loaded into the capillary. The Milli-GAT™ pump oscillated 1 μL of fluid at 2 μL s$^{-1}$ for 202 strokes in 60 minutes. Each time a particulate crossed the laser relative to when the command to start moving the pump was issued, the peak height, and a slit-scan of each particulate were recorded by a custom LABVIEW program.

Experiment 4. Tracking Multiple Living Cells.

Figure 9A:
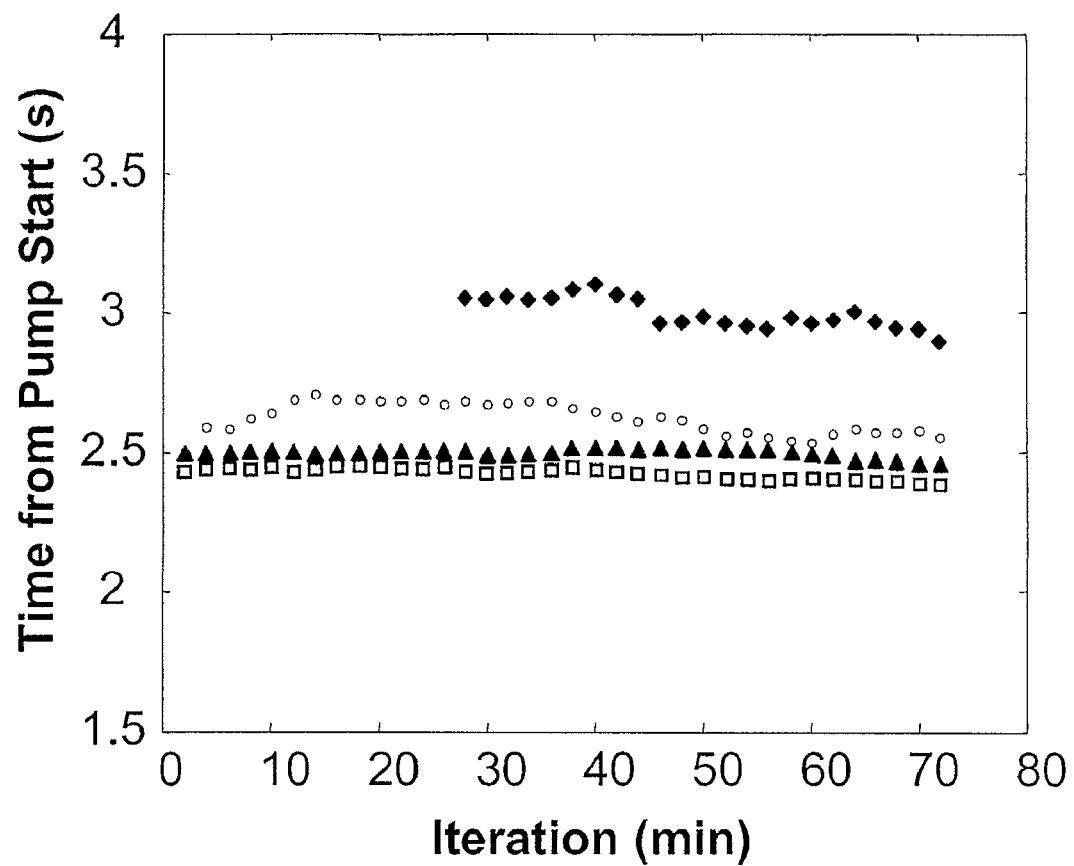
FIG. 9A is a chart of PA data for a plug of four yeast cells tracked over a period of approximately 70 minutes.

FIG. 9A is a chart of PA data for a plug of four yeast cells tracked over a period of approximately 70 minutes. For this experiment, a strain of Saccharomyces cerevisiae D603 cells were grown in YPD medium in a shake flask at 30° C. The cells were then diluted with fresh YPD medium and pumped into the capillary. The chart shows the detection of individual yeast cells in the measurement area over time (chart abscissa) measured as a function of time from when the pump was activated to move the plug in first and second directions (chart ordinate). The data show that the cells substantially maintain their relative position during the oscillation of the fluid back and forth across the measurement area. In one embodiment of this experimental approach, each cell can be labeled with a label or other marker, enabling tracking of individual cells within the plug.

Figure 9B:
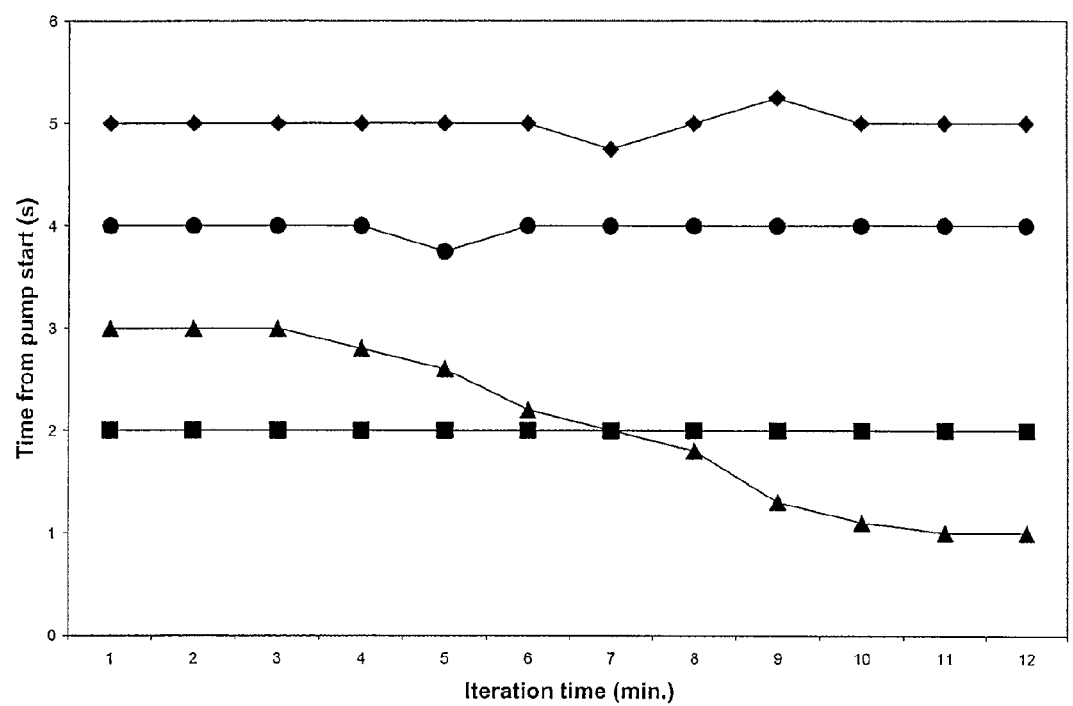
FIG. 9B shows a hypothetical chart illustrating an effect of measuring individually-identifiable particulates.

FIG. 9B shows a hypothetical chart illustrating an effect of measuring individually-identifiable particulates (in this case, the particulates are living cells). The data points in FIG. 9B can represent four different cells that may be uniquely identified by a PA system, for example, by labeling each cell with a label that fluoresces at a particular wavelength. Each point in FIG. 9B has a shape, i.e., square, triangle, circle, and diamond, to identify a particular cell. In this hypothetical example, the cell corresponding to the triangle series may be undergoing growth, for example, and thus the cell may be undergoing a transition from one streamline to another. This may cause the cell to slow down (or speed up) relative to the other cells in the plug. FIG. 9B shows that the changing cell (triangle series) has re-ordered with respect to neighboring cells (square and circle series), yet the PA can still track the position of the cell. In some embodiments, characteristics of the curve corresponding to the region where the cell transition took place can be used to infer cellular characteristics, such as growth rate and population balance equations.

Figure 9C:
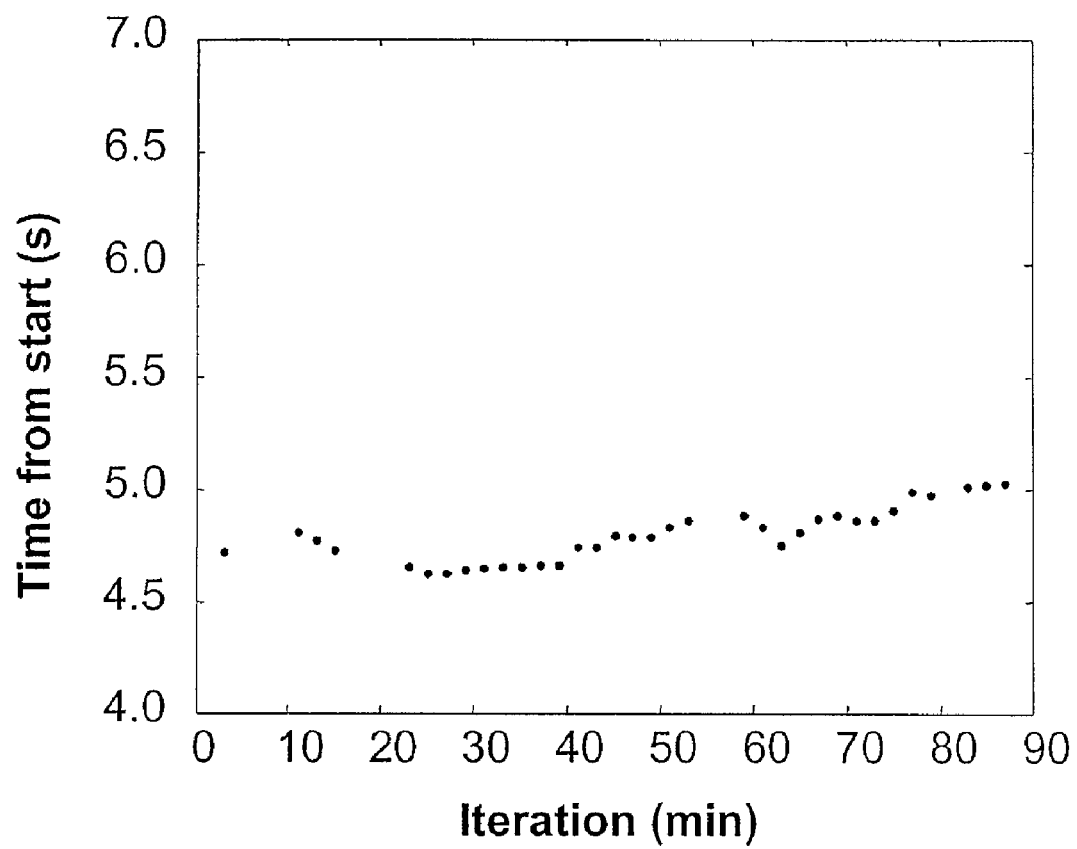
FIG. 9C shows PA data for a single Saccharomyces cerevisiae D603 yeast cell.
Figure 9D:
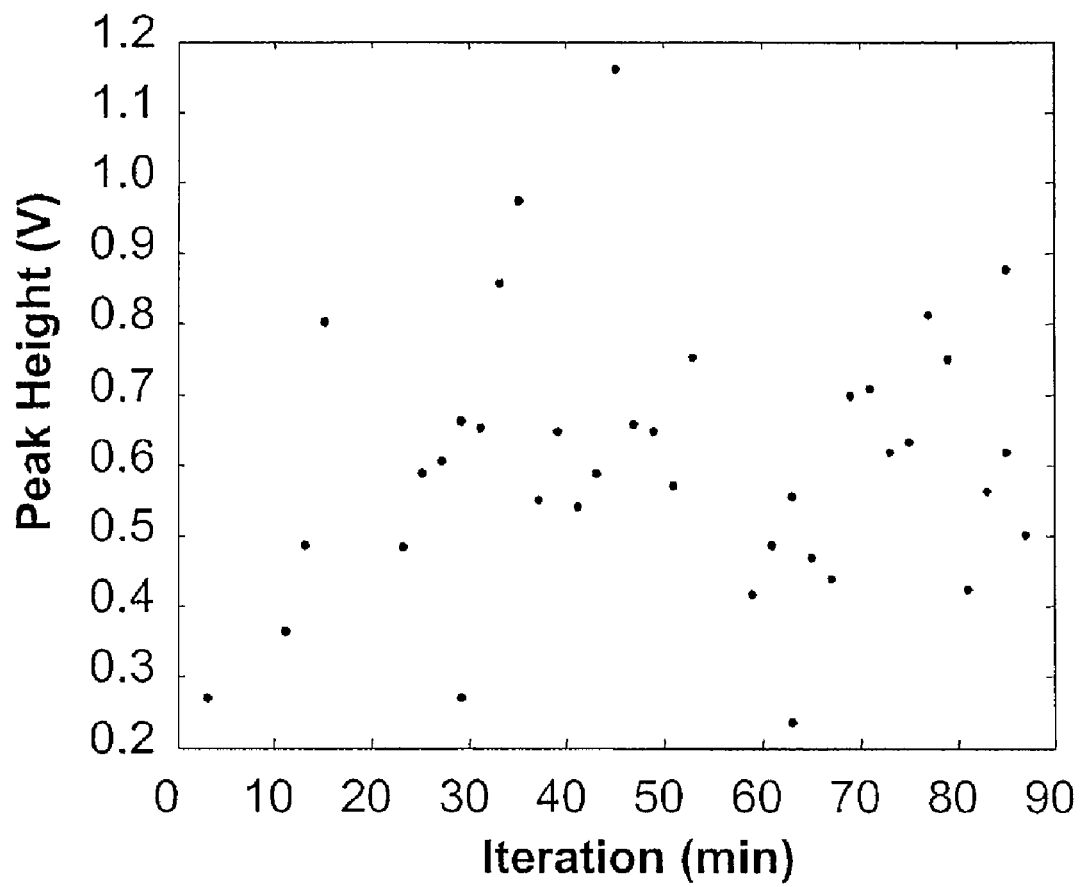
FIG. 9D shows PA data for a single Saccharomyces cerevisiae D603 yeast cell.

FIGS. 9C and 9D show PA data for a single Saccharomyces cerevisiae D603 yeast cell. The data in FIG. 9D show randomly varying peak heights which could be due to misalignment of the optical detector system used in the experiment.

Experiment 5. Spatial Variation in Detection Point.

When a laser beam is used to probe particulates, the beam can have a Gaussian intensity across each axis of an ellipse that makes up the measurement area. In some implementations, it may be advantageous to utilize only approximately a center portion of the Gaussian beam (e.g., ⅛ of the center) where the laser intensity varies only slightly. By expanding the beam to a larger width, less of the beam may be used, but the beam may be more homogeneous.

Figure 11:
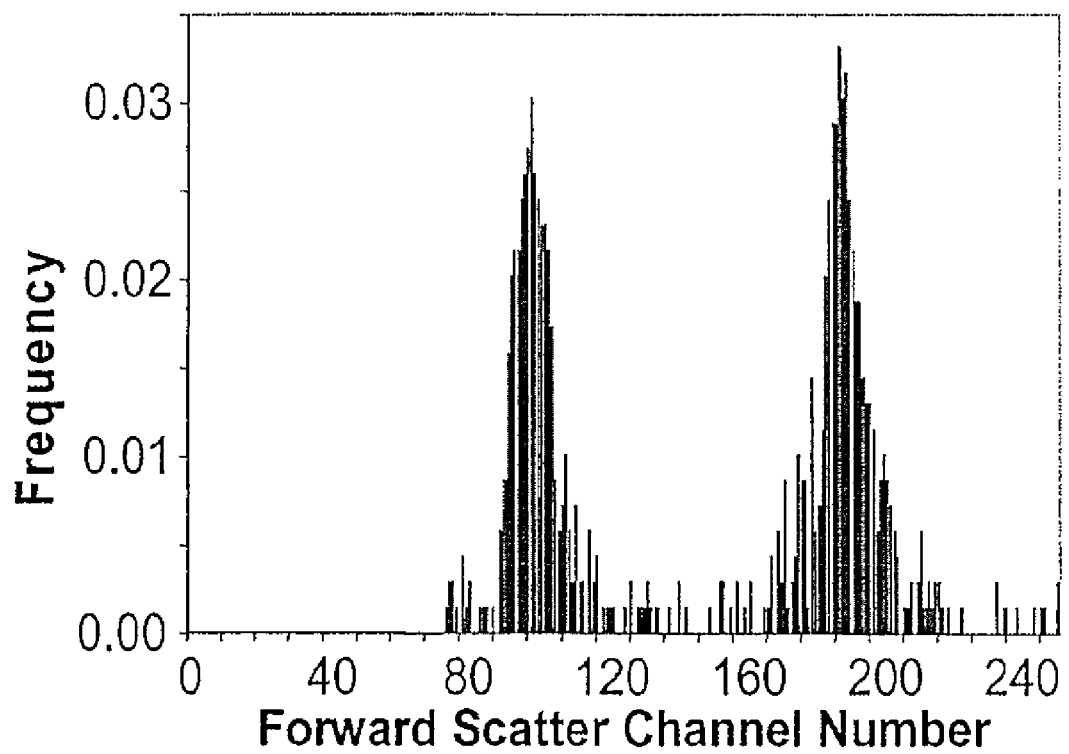
FIG. 11 is a histogram of frequency vs. forward scatter channel number detected in a PA apparatus.

An elliptical laser field approximately 5 µm×760 µm was focused on a 100 µm capillary, allowing repeat measurements of the same cell with a signal variance that reflects the histograms shown in FIG. 11. Further expansion of the beam in the width dimension is expected to result in smaller coefficients of variance of these peaks.

Experiment 6. Pumping Considerations.

In some embodiments, a sensitive flow sensor can be placed in-line with the flow-stream that measures fluid velocity as a function of time. This measurement may provide a basis for accurate pumping and control of the fluid and particulates in the stream. The reproducible oscillatory velocity pattern in the up and down direction is shown in FIG. 12A.

Figure 12:
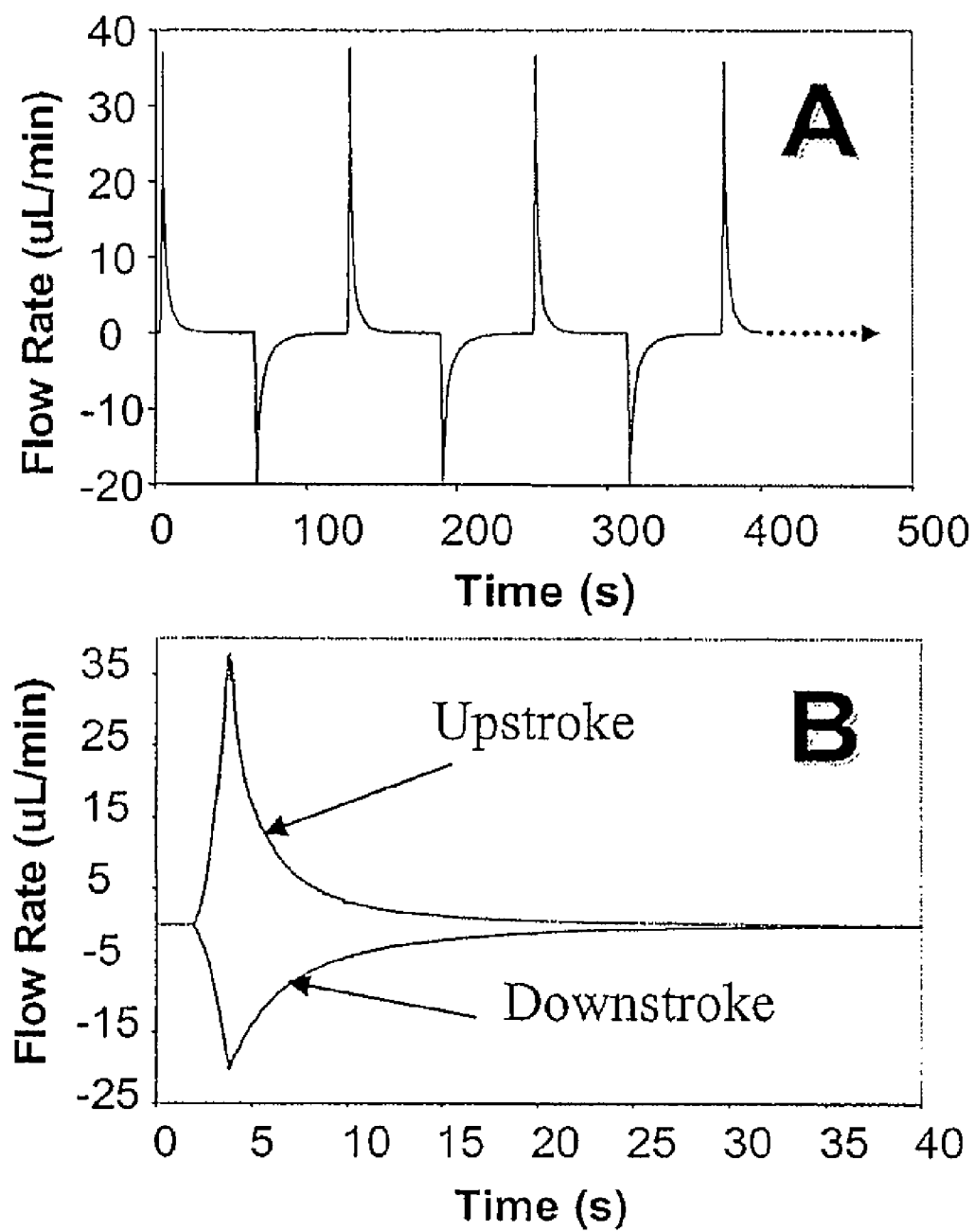
FIG. 12 is a plot of fluid velocity vs. time from a PA apparatus.

The flow sensor measurements revealed that the pumping is in fact highly reproducible as shown in FIG. 12B, which shows 40 superimposed pump stroke traces, where each trace is virtually identical. In some implementations, a smaller fluid volume may be supplied by a two pump system that may reduce relaxation time of the fluid after the pump stops. This slow relaxation may be due to delayed pressure relaxation due to the compressibility of the fluid.

Experiment 7. Polystyrene Particulates.

Figure 13:
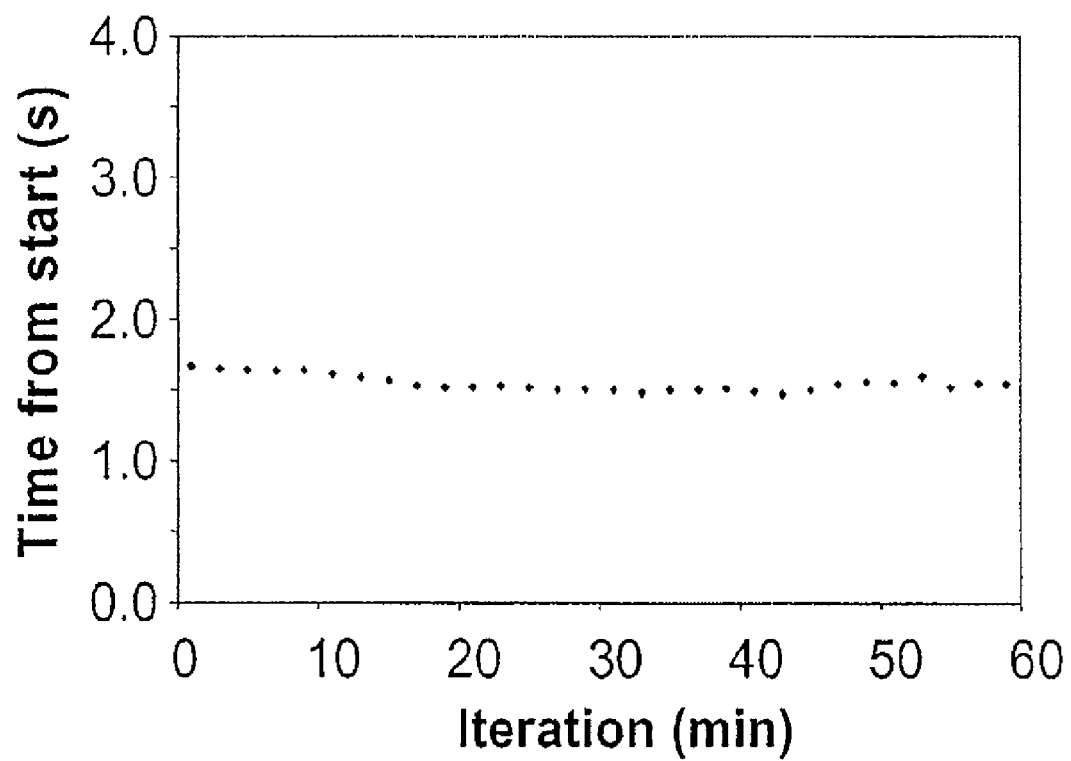
FIG. 13 is a plot showing tracking of a 15 μm particulate over time.

The reproducibility of a PA system was tested using monodisperse polystyrene particulates of 6, 10, 15, and 20 µm diameter. FIG. 13 shows tracking data for a 15 µm particulate over a period of one hour using a pump stroke length approximately equal to 200 nL. The data show that particulates do not diffuse significantly in the radial direction, which would be indicated by a particulate moving into a different stream line (i.e., changing velocity) due to the parabolic velocity profile of the fluid. To quantitate the difference between neighboring strokes, the relative distances were determined and the frequency distribution function of these distances was determined. The expected distribution from random diffusion of particulates in the radial direction distances were computed in a Monte Carlo simulation (FIG. 14) which shows that the Segre-Silberberg effect becomes clearly evident. The experimental distances are much narrower distributed than the expected distribution possibly due to random diffusion. The experimentally determined distribution may be expected to become even narrower for higher fluid velocities, as theory predicts the possibility of better focusing into a specific streamline. The experimentally determined distribution is not centered on the origin but shifted toward positive time. This may be due to particulate settling velocity that causes the trajectories to be slightly sloped. This slope could be eliminated by increasing the density of the fluid to the value of the particulate density. In one embodiment of a PA, density distributions of particulate populations can be determined based on the slope of the trajectories representing settling velocities.

Figure 14:
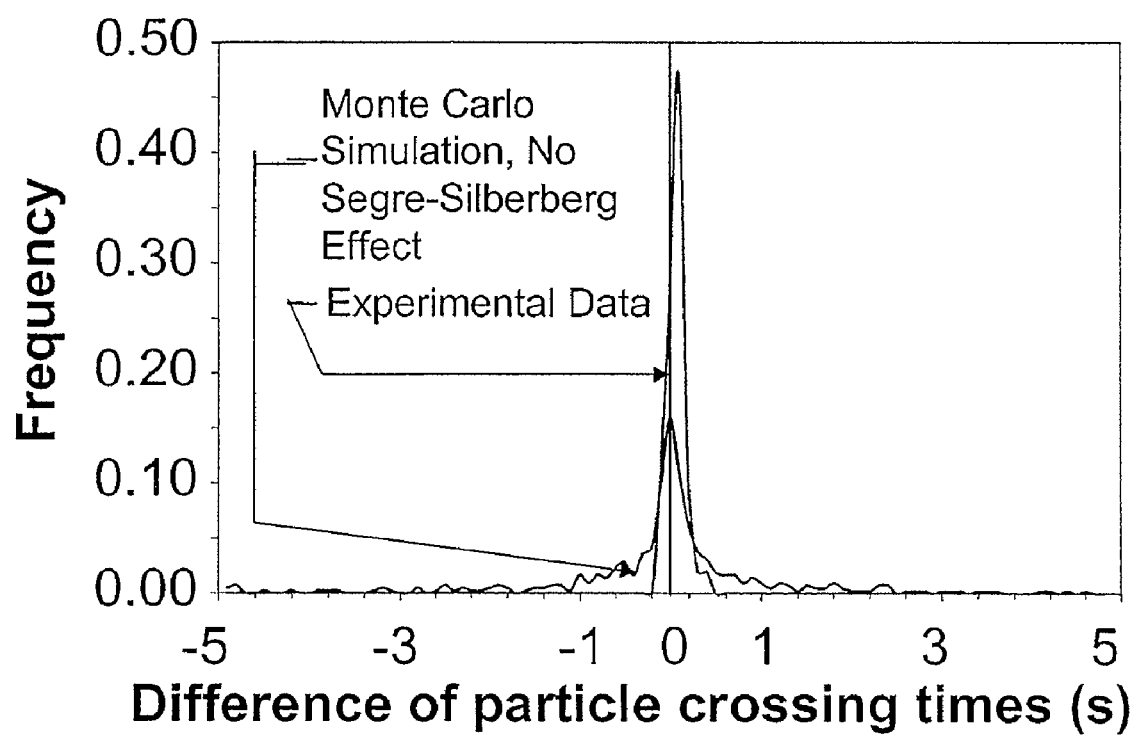
FIG. 14 shows distributions of relative distances particulates move between two pump strokes in a PA apparatus.

The data in FIGS. 13 and 14 can also provide a basis for estimating the maximum number of particulates that could be tracked over time based on their occurrence in the laser beam. A minimum distance between two particulates should have is the maximum distance that particulates can move between two strokes. This distance in this example is 2 mm. Assuming that all particulates are equally spaced in a plug of ordered cells that extends over 25 cm, this means that 125 particulates could be tracked on the basis of timing information alone. There may be additional criteria that help to identify particulates during tracking.

Experiment 8. Particulate Mixtures.

Figure 15:
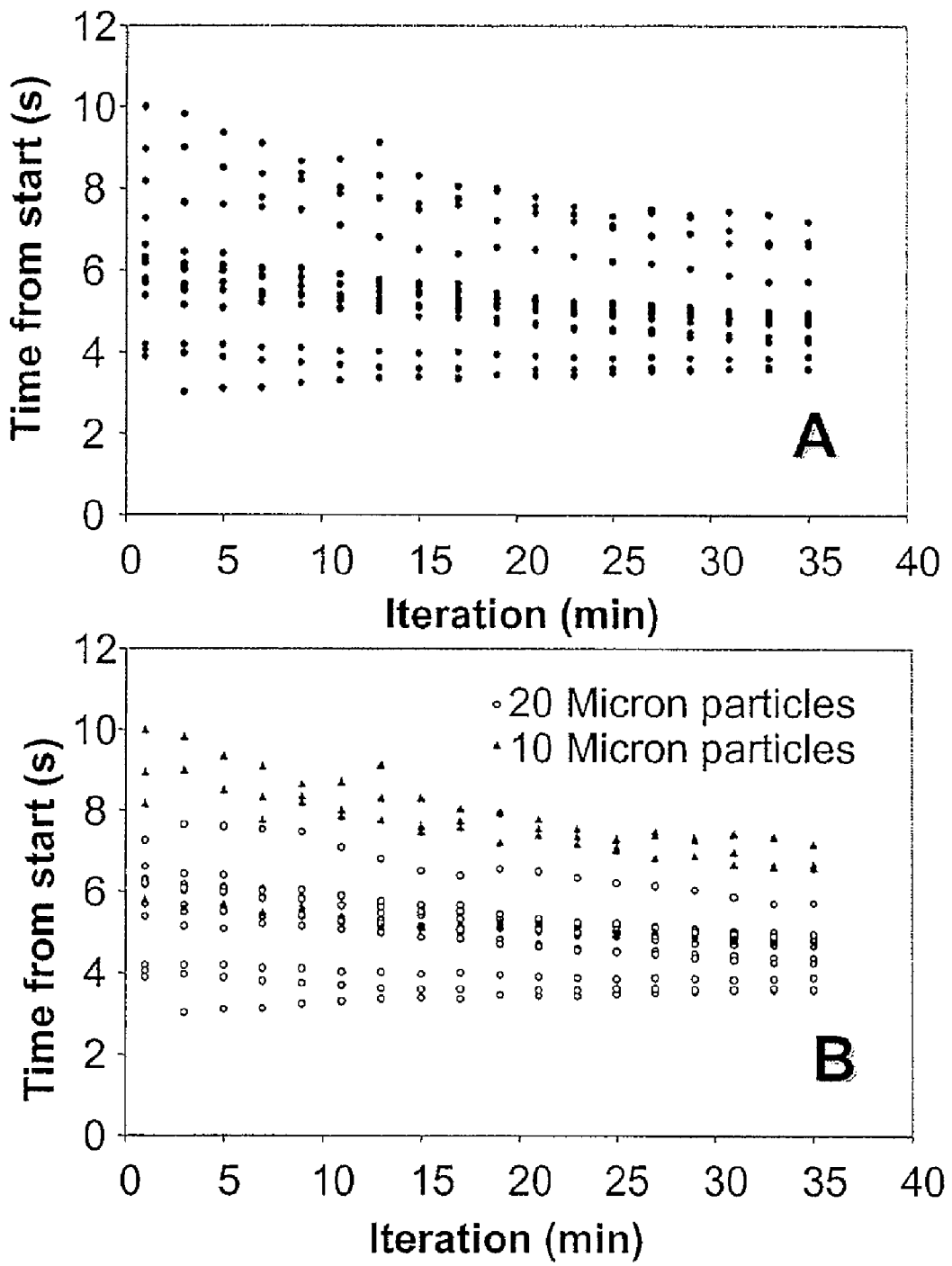
FIG. 15 shows tracking of particulate mixtures from a PA apparatus.

A PA was used to track of a mixture of particulates as presented in FIG. 15A. A mixture of 17 particulates consisted of four 10 µm particulates and thirteen 20 µm particulates. FIG. 15B shows that the tracking at this particulate density (in this case 1.05 g/L) becomes less clear based on the timing information alone. However the identification of individual particulate tracks is possible if the individual particulate properties as reflected in the measured signals are taken into account. The light scattering signals from 10 µm and 20 µm particulates are significantly different. If the tracking data are gated according to the signal intensity of 10 µm particulates then these particulates can be clearly differentiated from the 20 µm particulates. The corresponding tracks are shown in FIG. 15B.

While this example is useful to illustrate how tracks of individual particulates in more densely populated ordered cell sections can be determined, it also illustrates how this approach can be extended to cell populations. In real cell populations where cell characteristics vary over a measurable range, it may be advantageous to facilitate tracking. Tracking should be possible as long as neighboring cells in a section of a plug are sufficiently different from each other.

Experiment 9. Fluid Flow Between Sections.

Figure 16:
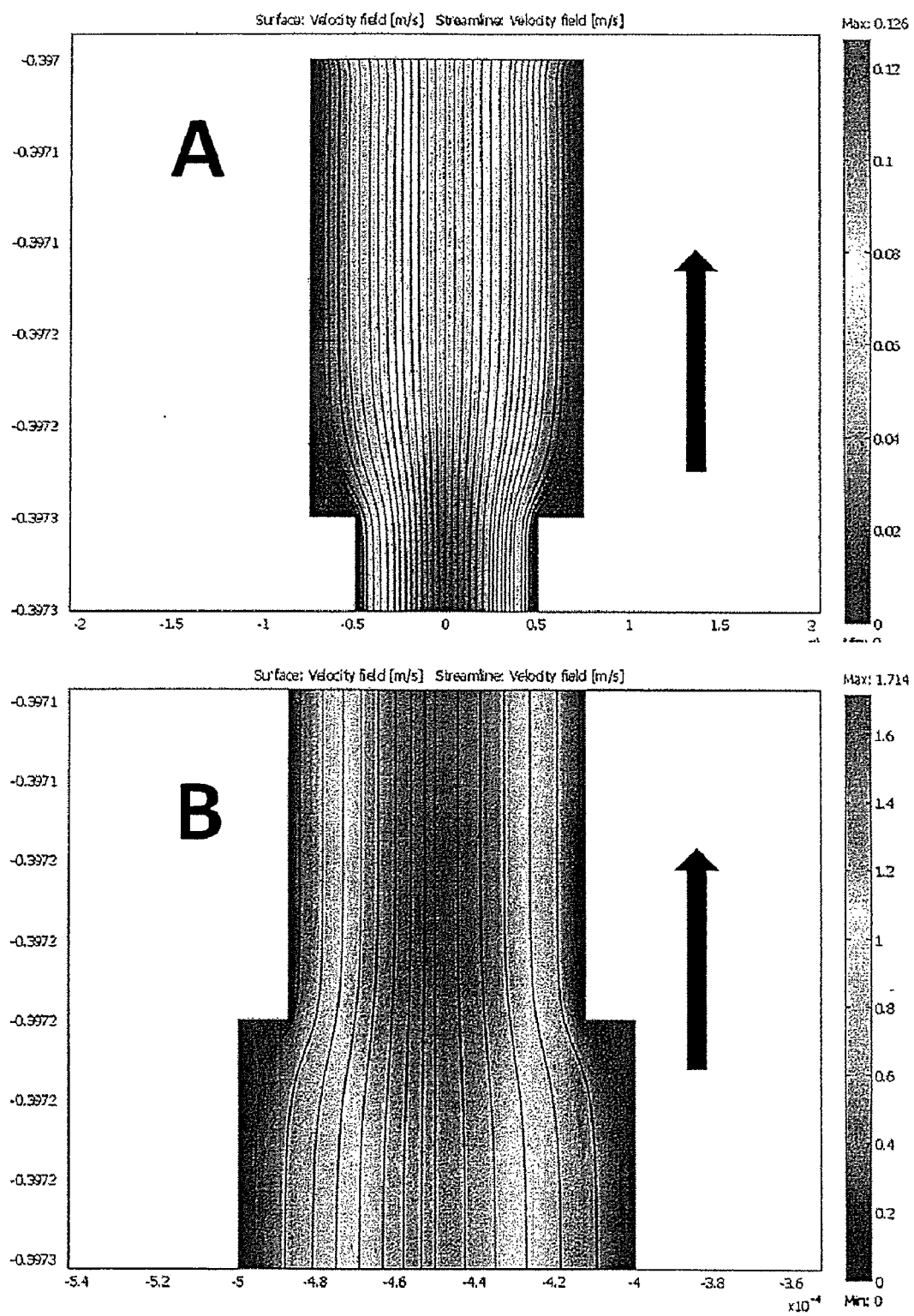
FIG. 16 shows a particulate velocity profile for capillary expansion and contraction.

In embodiments where the flow cell consists of a glass capillary adjacent to a porous hollow fiber to permit exchange of solutes in the capillary, it may be necessary to ensure that fluid flow is not perturbed in the capillary. Turbulence within the capillary can course destroy the ordering of cells. Fluid dynamic simulations of the junction between the glass capillary and the porous region were carried out for the case where the two diameters do not match precisely. FIG. 16 shows the velocity profiles with selected stream lines at the capillary/porous region junction when the capillary expands (a) and when it contracts (b). The majority of stream lines remain intact and some near the wall display slightly different behavior. This region is not expected to affect streamlines of interest that are at a distance of 0.6 times the radius or more from the capillary wall. Simulations have been performed for a Reynolds number of 10 and showed that the streamlines are still laminar and not expected to affect the position of the particulates. Real experiments may have a lower value. A significant turbulence can be observed for Reynolds numbers larger than 2300. Thus, turbulence due to an imperfect junction between the glass region and the porous regions will not likely affect particulate ordering.

Experiment 10. Particulate Settling Velocity.

Figure 17:
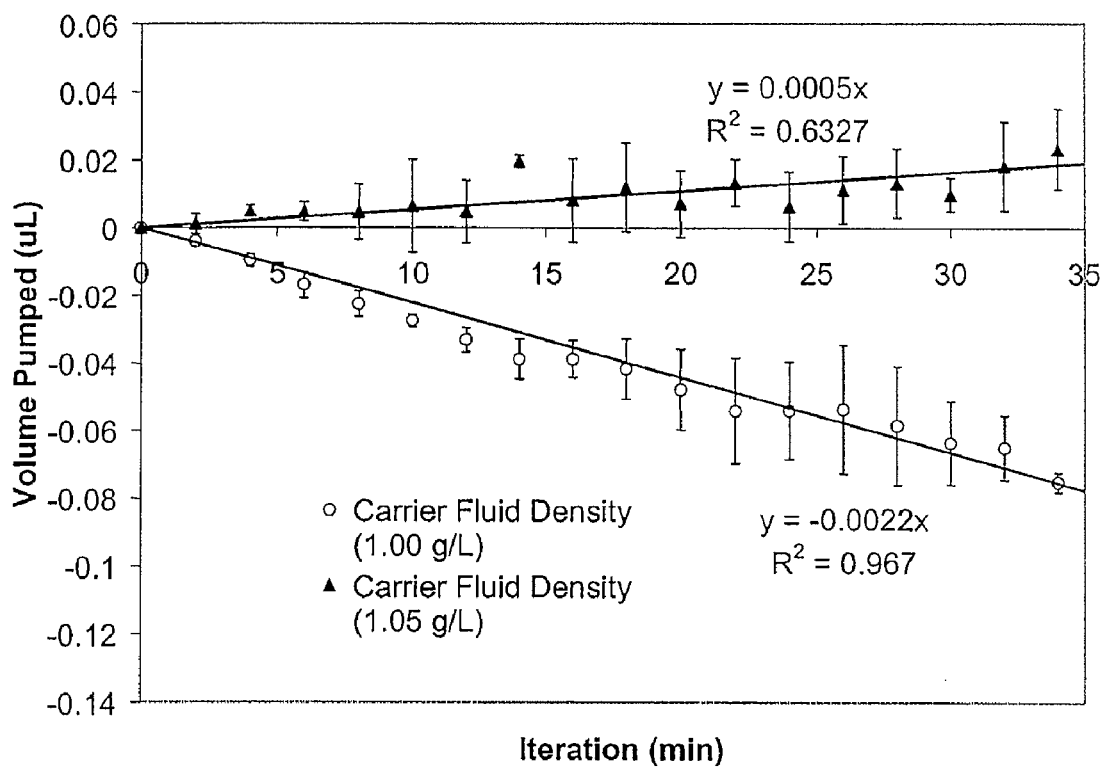
FIG. 17 is a plot of fluid volume movement versus time in a PA apparatus.

As discussed above, the PA can allow the determination of the density distribution of particulate populations from measured settling velocities. If the density of the particulates is higher than the fluid medium then the particulates are expected to settle during the oscillatory movement of the fluid. Likewise, if the density is less than the fluid then the particulates would be expected rise. Such an effect may be realized if the position of particulates is determined in terms of a true distance in the capillary expressed as a volume amount pumped. This distance can be obtained by transforming the time coordinate of the particulates into a volume using the velocity information. The velocity information can be provided by a flow sensor as described above and can be important because particulates detected during the pressure relaxation period can move much slower than particulates detected during active pumping as shown in FIG. 17.

Experiment 11. Tracking Cell Doublets.

Figure 18:
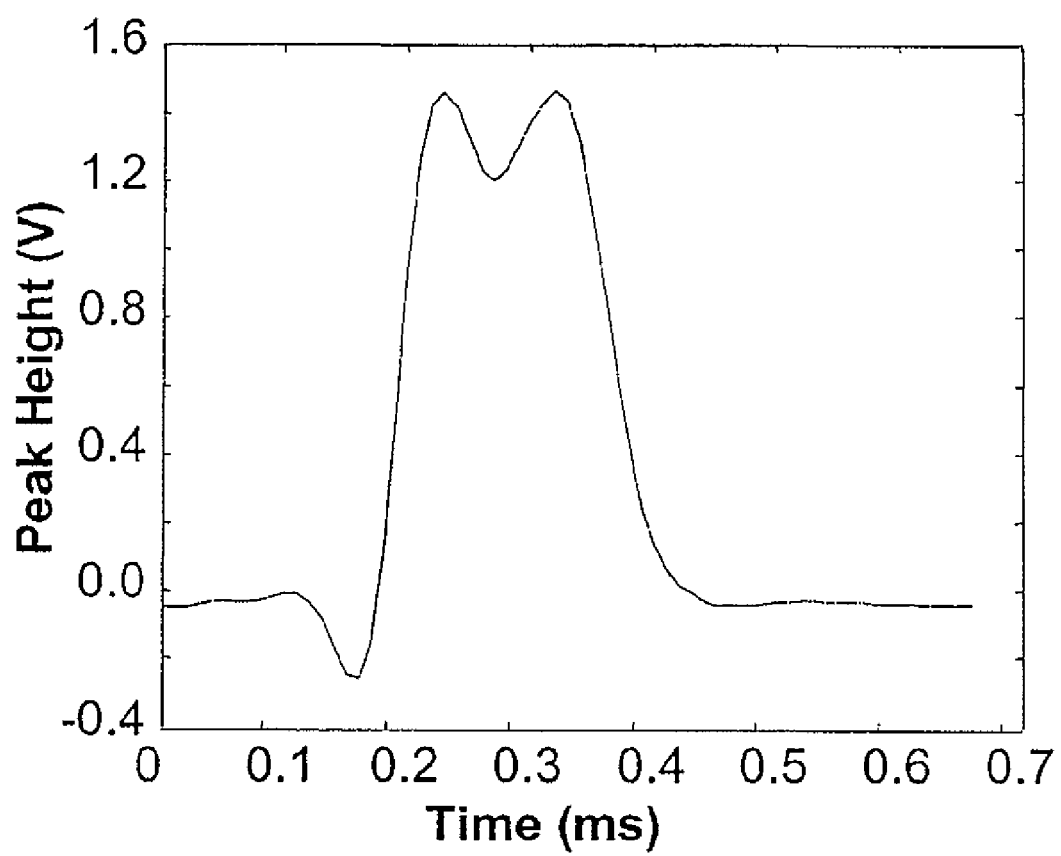
FIG. 18 is a plot showing tracking of a CHO cell from a PA apparatus.

Cells undergoing cell division may be expected to appear as particulate doublets as the division progresses. In some cases it can be possible to determine the partitioning function of cell components as cell division occurs. FIG. 18 shows PA data on CHO cells suspended in buffer solution. In this experiment, a cell doublet was scanned for over 70 minutes. The relative magnitude of the two modes remained substantially constant over the 70 minute period where a single scan was recorded once every minute. The data suggest that oblong particulates are in fact oriented along their longitudinal axis and that estimation of the two cell portions via slit scanning using a PA apparatus to track cell doublets should be feasible.

Experiment 12. Particulate Interference.

According to the Segre-Silberberg effect particulates of differing radii can migrate to their respective equilibrium radii when exposed to a parabolic velocity profile. Since each equilibrium radius has an associated axial velocity, particulates of differing radii can have differing velocities and therefore, move different axial distances when exposed to parabolic flow. Thus, different sized particulates have the potential to cross past each other and interfere with the equilibrium radii of the interacting particulates. This is especially relevant when considering a population of cells, as cell sizes are distributed over a range of cell sizes.

There are two possibilities to how the particulate size distribution can effect the operation of the proposed single-cell tracking instrumentation. The first possibility is that if crossing events occur, they would be completely reversible due to the fact that the particulates would be in different locations in the radial plane. Therefore, particulates would be able to cross each other and not disturb the final axial location of the particulate. The second possibility is if crossing events cause irreversible changes in final axial position of an interacting particulate. If this is true, then crossing events must be eliminated. As a worst case scenario, the second possibility is assumed to be the only one to occur, and the maximum number of cells that could be analyzed is calculated. First, to reflect the worst case suspension of cells, a system is devised where two particulates, one particulate twice as massive as the second exist in the instrument ($r_1$=10 µm, $r_2$=13 µm).

Figure 19:
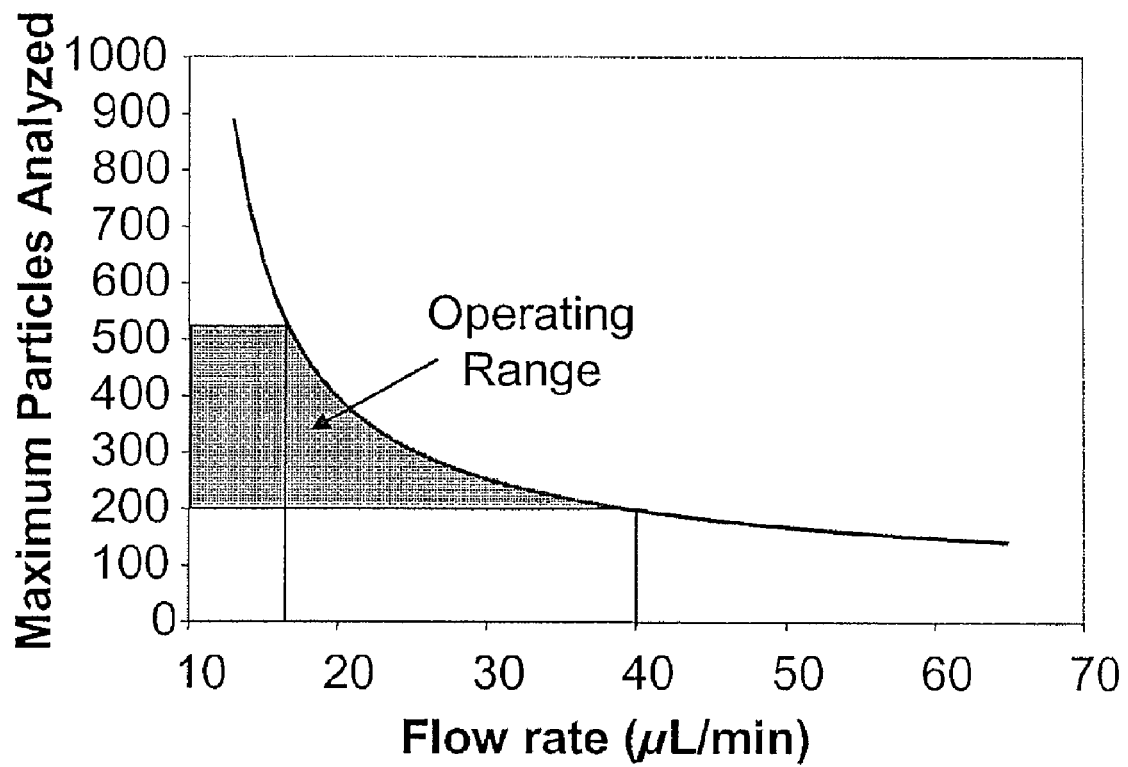
FIG. 19 indicates a desired operating range as a function of particulates analyzed and flow rate, according to one embodiment.

Next, the respective equilibrium radii and velocity of these two particulates were calculated from a numerical simulation given a flow rate of the system (33, 50). Then, with the calculated velocity difference between the two cells, the minimum initial distance between the particulates is calculated so that at the end of the stroke, the two particulates would be one particulate diameter apart from each other. During this derivation all terms involving the stroke length and pumping time drop out making this applicable to all possible stroke lengths. Next, the upper limit of cells in this absolute worst case scenario is calculated by filling the capillary with particulates the minimum distance apart, and the results are plotted in FIG. 19. As can be seen in this plot, even in the worst case scenario, a sizable number of cells that would accurately reflect the behavior of the population can still be analyzed. As seen in FIG. 19, it appears that even when different sized particulates cross each other, the crossing event is reversible, and does not lead to significant variances in the time each particulate crosses the laser, and thus should not affect the tracking.

Experiment 13. PA Using a Capillary-Waveguide.

Figure 20:
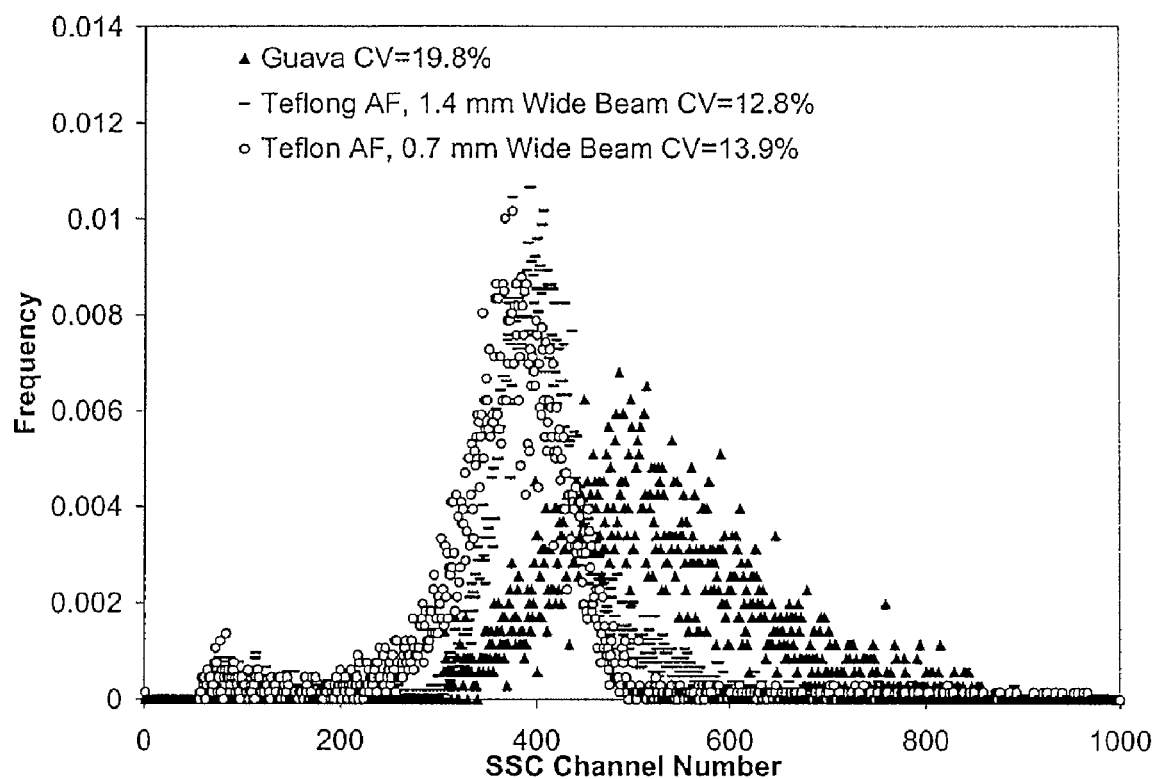
FIG. 20 is a chart showing a distribution of side scatter peak height signals using a capillary-waveguide PA.

To examine the suitability of a Teflon AF capillary for use as a capillary-waveguide, 2 µm polystyrene beads were pumped through the capillary. Light was transferred from the distal end of the capillary to a PMMA fiber optic cable of 1 mm core diameter by placing the distal end of the capillary in close proximity to the fiber optic. The other end of the fiber optic was directed into a photomultiplier tube where the amount of scattered light was measured. FIG. 20 shows a distribution of side scatter (SSC) peak height signals from 2 µm polystyrene beads. Signal quality was assessed by the coefficient of variation (CV, standard deviation/mean*100) with a high quality signal having a smaller CV. SSC signals were collected from a commercially available Guava cytometer with traditional light collection optics and compared to SSC signals collected using the Teflon AF waveguide illuminated by 488 nm light focused at two different beam widths. The signals collected using the Teflon AF capillary showed significantly decreased CV values when compared to the Guava cytometer. Further beam expansion yielded a slightly improved CV.

Waveguide-PA Fluorescence Detection

Figure 21:
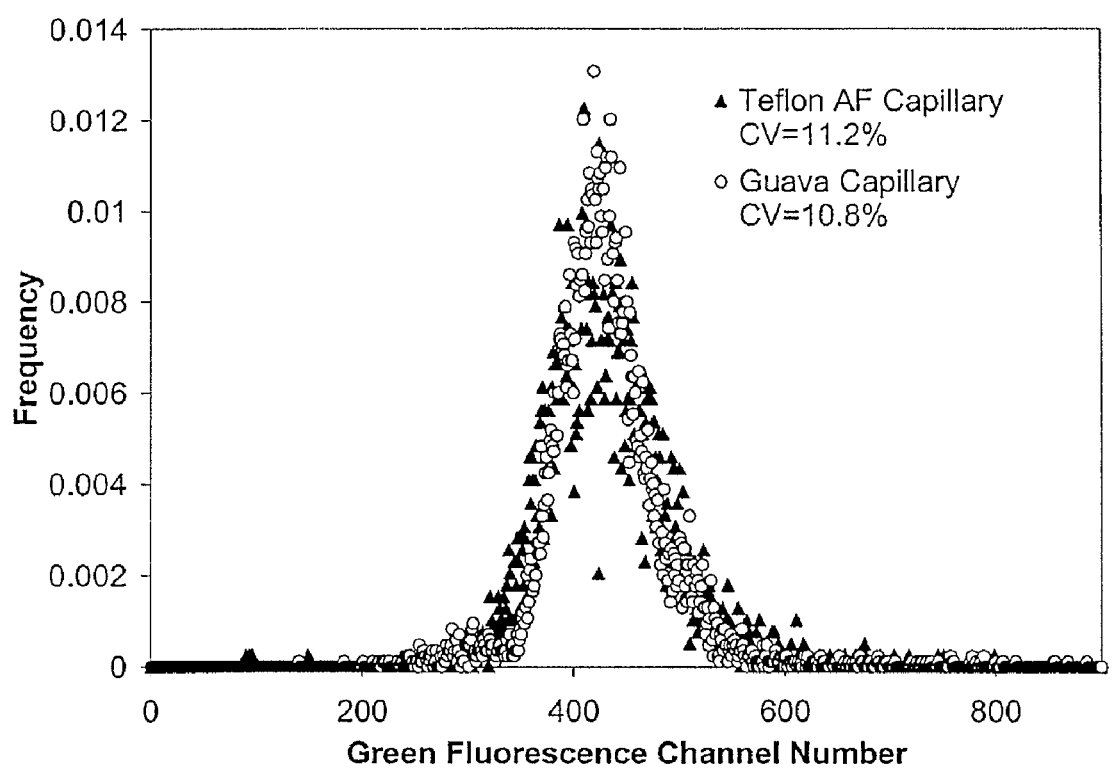
FIG. 21 is a chart of the distribution of green fluorescence from 6 μm particulates collected using a PA with a Teflon capillary-waveguide Like reference symbols in the various drawings indicate like elements.

Six micron polystyrene particles containing the fluorescent dye Bodipy (Alignflow Plus, Invitogen, Carlsbad Calif.) were detected in a PA using a Teflon capillary-waveguide. FIG. 21 is a chart of the distribution of green fluorescence detected from the particulates. The data are compared to the same particulates using a commercially-available Guava cytometer using conventional cytometry optics, e.g., by measuring the fluorescence at an angle to the interrogating laser beam. The particulates were excited with approximately 10 mW of 488 nm laser light. A 515 nm cutoff filter was used to filter out 488 nm light scattered directly from the particulates.

A number of embodiments of the invention have been described. Nevertheless, it will be understood that various modifications may be made without departing from the spirit and scope of the invention. For example, multiple laser beams can be employed and directed at a given measurement area to provide spectroscopic flexibility in measurements. Alternatively, multiple measurement areas can be configured as vertically "stacked" layers within the capillary. This embodiment can provide, for example, multiple detection scenarios for fluorescent labels having unique photo-excitation properties. Furthermore, a secondary measurement area can exist along the capillary, and after a flow switch, for example intersection 305 in FIG. 3, so that further analysis of particulates can be performed on particulates that are not removed from the primary fluid flow.

The detection apparatus may be configured in a "backward-scattering" arrangement, rather than forward, or side-scattering, using optical configurations that are known in the art. The number of cells that can be tracked using the described methods is not limited, and in preferred embodiments, a PA can track thousands of cells. While the orientation of the capillary has been generally described as vertical, the capillary can be configured to allow flow along a horizontal axis.

Accordingly, other embodiments are within the scope of the claims that follow.

REFERENCES

Block D E, Eitzman P D, Wangensteen J D, Srienc F. (1990). Slit scanning of Saccharomyces cerevisiae cells: quantification of asymmetric cell division and cell cycle progression in asynchronous culture. Biotechnol Prog. November-December; 6(6):504-12.

Fredrickson A C; Ramkrishna D and Tsuchiya H M. (1967). Statistics and Dynamics of Procaryotic Cell Populations. Math Biosci., 1:327-374.

Joseph, D. D., Ocando, D. (2002). Slip Velocity and Lift. J. Fluid Mech. 454, 263-286.

Leighton and Acrivos. (1985). The Lift on a Small Sphere Touching a Plane in the Presence of a Simple Shear Flow. Z. Agnew. Math Phys., 36, 174-178.

Li H., Lu X., Fang H., and Qian Y (2004). Force evaluations in lattice Boltzmann simulations with moving boundaries in two dimensions. Physical Review E, 70, 026701.

Matas J P, Morris J F, and Guazelli E. (2004). Inertial migration of rigid spherical particulates in Poiseuille flow. J. Fluid Mech. vol. 515, pp. 171-195.

Melamed M R, Lindmo T, and Mendelsohn M L. (1994). Flow Cytometry and Sorting Wiley-Liss, New York.

Ramkrishna D. (2000). Population Balances: Theory and Applications to Particulate Systems in Engineering, Academic Press; 1st edition.

Segrè, G., Silberberg, A. (1961). Radial Poiseuille flow of suspensions. Nature 189, 209.

Segrè, G., Silberberg, A. (1962). Behavior of macroscopic rigid spheres in Poiseuille flow: Part I. J. Fluid Mech. 14, 136-157.

Shapiro, H. M. (1985). Practical flow cytometry. New York: Alan R. Liss, Inc.

What is claimed is:

1. A system for analyzing one or more particulates, the system comprising:
    a capillary having a lumen configured for fluid flow and comprising a fluid, the capillary having an index of refraction less than a refractive index of said fluid, and configured to guide light energy scattered or emitted from one or more particulates when present in the fluid to a light energy collection assembly located distal to a measurement area;
    an energy source that imparts light energy to the measurement area;
    one or more particulates present within said fluid; and
    a pump system configured to apply a selectable pressure to an end of the capillary to cause the one or more particulates present in said fluid to move back and forth across the measurement area such that the one or more particulates both 1) organize into discrete streamlines and 2) remain in the streamlines during back and forth movement through the measurement area.

2. The system of claim 1, wherein the light energy is from a laser.

3. The system of claim 1, wherein capillary is a hollow-bore waveguide.

4. The system of claim 1, further comprising a coupler fixedly attached to the capillary, wherein the coupler provides fluid flow from the capillary to a tube that flows the fluid away from the capillary, and also provides for the energy to be transmitted from the capillary to an energy conduit.

5. The system of claim 4, wherein the energy conduit is a fiber-optic waveguide that transmits light energy from the coupler to a light detector.

6. The system of claim 1, wherein the one or more particulates comprise cells.

* * * * *

UNITED STATES PATENT AND TRADEMARK OFFICE
CERTIFICATE OF CORRECTION

| | | |
|---|---|---|
| PATENT NO. | : 8,409,509 B2 | Page 1 of 1 |
| APPLICATION NO. | : 12/102851 | |
| DATED | : April 2, 2013 | |
| INVENTOR(S) | : Srienc et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 868 days.

Signed and Sealed this
Seventh Day of October, 2014

Michelle K. Lee
*Deputy Director of the United States Patent and Trademark Office*